United States Patent
Kim et al.

(10) Patent No.: US 9,288,556 B2
(45) Date of Patent: Mar. 15, 2016

(54) METHOD AND APPARATUS FOR MEASURING BODY BALANCE OF WEARABLE DEVICE

(71) Applicant: ZIKTO, Seoul (KR)

(72) Inventors: Kyung Tae Kim, Seoul (KR); Sung Hyun Kim, Seoul (KR); David Han Suk Suh, Seoul (KR)

(73) Assignee: ZIKTO, Seoul (KR)

(*) Notice: Subject to any disclaimer, the term of this patent is extended or adjusted under 35 U.S.C. 154(b) by 0 days.

(21) Appl. No.: 14/845,226

(22) Filed: Sep. 3, 2015

(65) Prior Publication Data

US 2015/0382086 A1 Dec. 31, 2015

Related U.S. Application Data

(63) Continuation-in-part of application No. PCT/KR2015/006186, filed on Jun. 18, 2015, and a continuation-in-part of application No. 14/547,576, filed on Nov. 19, 2014.

(30) Foreign Application Priority Data

| Jun. 18, 2014 | (KR) | 10-2014-0074521 |
| Oct. 2, 2014 | (KR) | 10-2014-0133167 |
| Oct. 2, 2014 | (KR) | 10-2014-0133171 |
| Jun. 17, 2015 | (KR) | 10-2015-0086216 |

(51) Int. Cl.
*G08C 19/22* (2006.01)
*H04Q 9/00* (2006.01)
(Continued)

(52) U.S. Cl.
CPC .............. *H04Q 9/00* (2013.01); *H04B 1/385* (2013.01); *H04W 4/02* (2013.01); *A61B 5/00* (2013.01); *A61B 5/0002* (2013.01); *A61B 5/112* (2013.01); *A61B 5/1116* (2013.01)

(58) Field of Classification Search
USPC ...................................... 340/870.07; 600/595
See application file for complete search history.

(56) References Cited

U.S. PATENT DOCUMENTS

| 8,738,925 B1 * | 5/2014 | Park | H04B 7/26 380/270 |
| 8,842,887 B2 * | 9/2014 | Beatson | G06F 21/32 382/115 |

(Continued)

FOREIGN PATENT DOCUMENTS

| JP | 2003-093566 A | 4/2003 |
| JP | 2008-167899 A | 7/2008 |

(Continued)

OTHER PUBLICATIONS

International Search Report and Written Opinion (issuance date: Sep. 30, 2015) issued by the Korean Intellectual Property Office (KIPO) for PCT Application No. PCT/KR2015/006186, filed on Jun. 18, 2015.

*Primary Examiner* — Jennifer Mehmood
*Assistant Examiner* — Rufus Point
(74) *Attorney, Agent, or Firm* — Snyder, Clark, Lesch & Chung, LLP

(57) ABSTRACT

A wearable device includes a communication unit that wirelessly communicates with a first external device; a motion sensor that senses the user's motion; and a control unit. The wearable device collects a first motion data generated by the user's motion and transmits the first motion data to the first external device, receives a first security level data and a second security level data from the first external device, and receives only the first security level data from the first external device when the wearable device is converted into a non-wearing state from a wearing state.

20 Claims, 14 Drawing Sheets

(51) Int. Cl.
*H04W 4/02* (2009.01)
*H04B 1/3827* (2015.01)
*A61B 5/11* (2006.01)
*A61B 5/00* (2006.01)

(56) References Cited

U.S. PATENT DOCUMENTS

| | | | | |
|---|---|---|---|---|
| 9,035,568 B2 * | 5/2015 | Ganton | ............... | H05B 33/0857 315/216 |
| 2005/0178201 A1 * | 8/2005 | Impio | ................... | A61B 5/0488 73/379.01 |
| 2007/0027585 A1 * | 2/2007 | Wulff | ...................... | G01P 13/00 701/1 |
| 2008/0183097 A1 * | 7/2008 | Leyde | .................. | A61B 5/0006 600/545 |
| 2011/0093210 A1 * | 4/2011 | Matsuzaki | ........... | A61B 5/0002 702/19 |
| 2011/0271964 A1 * | 11/2011 | Zhang | ...................... | A47G 9/10 128/845 |
| 2012/0212505 A1 * | 8/2012 | Burroughs | ......... | G09B 19/0038 345/629 |
| 2012/0251079 A1 * | 10/2012 | Meschter | ............ | G06F 19/3406 386/278 |
| 2012/0253233 A1 * | 10/2012 | Greene | ................ | A61B 5/7275 600/592 |
| 2012/0253234 A1 * | 10/2012 | Yang | .................... | A61B 5/1038 600/595 |
| 2013/0002533 A1 * | 1/2013 | Burroughs | .......... | G06F 19/3481 345/156 |
| 2013/0035613 A1 * | 2/2013 | Curtiss | ................. | A61B 5/6898 600/595 |
| 2013/0054180 A1 * | 2/2013 | Barfield | .............. | G01P 15/0891 702/138 |
| 2013/0178958 A1 * | 7/2013 | Kulach | ............... | A63B 24/0021 700/91 |
| 2013/0190658 A1 * | 7/2013 | Flaction | ............... | A61B 5/1038 600/595 |
| 2013/0278435 A1 * | 10/2013 | Ellis | ...................... | A43B 1/0054 340/870.07 |
| 2013/0338802 A1 * | 12/2013 | Winsper | .............. | G06F 19/3481 700/92 |
| 2014/0097967 A1 * | 4/2014 | Ellis | ...................... | A61B 5/1038 340/870.07 |
| 2014/0135955 A1 * | 5/2014 | Burroughs | .......... | G06F 19/3481 700/91 |
| 2014/0228988 A1 * | 8/2014 | Hoffman | ............ | A63B 71/0622 700/91 |
| 2014/0299775 A1 * | 10/2014 | Kimmel | ............ | G06K 9/00771 250/341.8 |
| 2015/0031348 A1 * | 1/2015 | Lee | ........................ | H04B 1/385 455/418 |
| 2015/0067811 A1 * | 3/2015 | Agnew | ................ | H04L 63/0807 726/9 |
| 2015/0106616 A1 * | 4/2015 | Nix | ..................... | H04W 52/0235 713/156 |
| 2015/0161374 A1 * | 6/2015 | Kim | ......................... | G06F 1/1694 726/19 |
| 2015/0227191 A1 * | 8/2015 | Pitigoi-Aron | ........ | A61B 5/0024 713/189 |
| 2015/0230183 A1 * | 8/2015 | Stogaitis | ........... | H04W 52/0254 455/574 |
| 2015/0234473 A1 * | 8/2015 | Wang | ...................... | G06F 3/017 345/156 |
| 2015/0272511 A1 * | 10/2015 | Najafi | ................... | A61B 5/7275 600/301 |

FOREIGN PATENT DOCUMENTS

| | | |
|---|---|---|
| KR | 10-2010-061353 A | 6/2010 |
| KR | 10-1219957 B1 | 1/2013 |

* cited by examiner

METHOD AND APPARATUS FOR MEASURING BODY BALANCE OF WEARABLE DEVICE

RELATED APPLICATIONS

The present application is a continuation-in-part of International Application No. PCT/KR2015/006186 filed on Jun. 18, 2015, which claims priority to Korean Patent Application No. 10-2014-0074521 filed on Jun. 18, 2014, Korean Patent Application No. 10-2014-0133167 filed on Oct. 2, 2014, Korean Patent Application No. 10-2014-0133171 filed on Oct. 2, 2014, and Korean Patent Application No. 10-2015-0086216 filed on Jun. 17, 2015, all of the preceding applications being incorporated by reference herein. The present application is also a continuation-in-part of U.S. patent application Ser. No. 14/547,576, filed on Nov. 19, 2014, which is also incorporated by reference herein.

BACKGROUND

1. Field of the Invention

The present invention relates to a method and apparatus for measuring a body balance of a wearable device.

2. Description of the Related Art

A smart band is a wristband that can retrieve various services, such as diary, messages, reports and stock quotations via a wireless communication. Also, users may download data depending on the service and may set their account in a web browser.

In recent years, as the interest in the smart band has increased, the need for health care services using the smart band has also increased.

SUMMARY

Aspects of the present invention provide a smart band that provides a body balance, i.e., asymmetric information of a body type, by measuring the motion of user's both arms.

Aspects of the present invention also provide a method for measuring the body balance of the smart band that provides the body balance, i.e., the asymmetric information of the body type, by measuring the motion of user's both arms.

Aspects of the present invention also provide a computer-readable recording medium that includes a program for executing the method for measuring the body balance of the smart band that provides the body balance, i.e., asymmetric information of the body type by measuring the motion of user's both arms.

The objects of the present invention are not limited to those mentioned above, and other problems which are not mentioned will be clearly understood by those skilled in the art from the following description.

According to an aspect of the present invention, there is provided a method for correcting a posture of the wearable device, the method comprising: wirelessly communicating with a portable electronic device; and receiving a first request signal of the portable electronic device.

At this time, the portable electronic device may be in a first security state.

The method for correcting a posture of the wearable device may further comprise collecting a first motion data generated by the user's motion through a motion sensor provided in the wearable device during a certain period of time or during collection of a certain amount of data; transmitting the first motion data to the portable electronic device; and receiving a second request signal of the portable electronic device.

At this time, the portable electronic device may be in a second security state.

The method for correcting a posture of the wearable device may further comprise collecting a second motion data generated by the user's motion through a motion sensor provided in the wearable device during a certain period of time or during collection of a certain amount of data; transmitting the second motion data to the portable electronic device; and receiving a third request signal of the portable electronic device.

At this time, the portable electronic device may be in a third security state.

The method for correcting a posture of the wearable device may further comprise collecting a third motion data generated by the user's motion through the motion sensor provided in the wearable device during a certain period of time or during collection of a certain amount of data; and transmitting the third motion data to the portable electronic device.

There is an advantage that it is possible to correct the posture of the body and receive a guide without additional circuits and separate operations of a user.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE EMBODIMENTS

Figure 1:
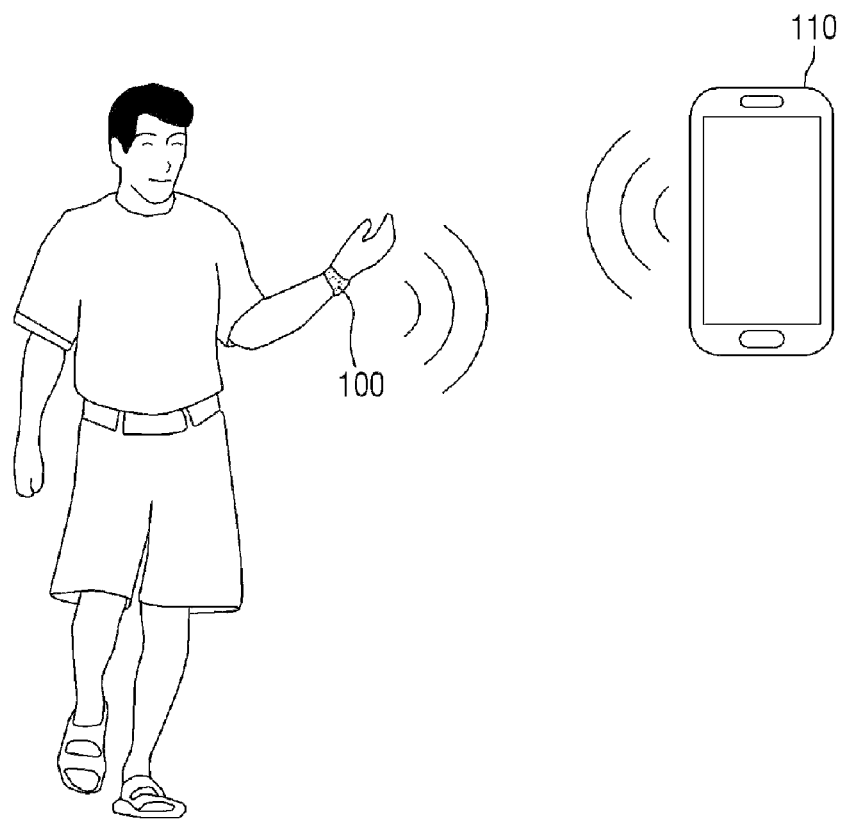
FIG. 1 is a diagram illustrating a wearable device according to an embodiment of the present invention and a smart phone connected thereto.

Advantages and features of the present invention and methods of accomplishing the same may be understood more readily by reference to the following detailed description of preferred embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Sizes and relative sizes of the components illustrated in the drawings may be exaggerated for clarifying the description. Same reference numerals throughout the specification refer to the same constituent elements, and "and/or" includes any and all combinations of one or more of the associated listed items.

It will be understood that when an element or a layer is referred to as being "on" or "over" another element or layer, it includes all the cases where the element or layer is directly on the other element or layer or other elements or other layers are interposed in the middle. In contrast, when an element is referred to as being "directly on" or "just above" another element or layer, it represents a case where other elements or layers are not interposed in the middle.

Spatially relative terms, such as "beneath," "below," "lower," "above," and "upper" may be used herein for ease of description to describe one element or feature's relationship to another elements or features as illustrated in the figures. It will be understood that the spatially relative terms are intended to encompass different orientations of the element in use or operation in addition to the orientation depicted in the figures. For example, if the element in the figures is turned over, elements described as "below" or "beneath" other elements or features would then be oriented "above" the other elements or features. Thus, the exemplary term "below" can encompass both an orientation of above and below. The element may be otherwise oriented at other orientations and the spatially relative descriptors used herein interpreted accordingly.

The terms used herein are intended to explain the examples and are not intended to limit the present invention. In this specification, the singular forms also include plural forms, unless specifically mentioned in phrases. The terms "comprising," and/or "including" does not preclude the presence or addition of one or more other components, in addition to the mentioned constituent elements.

It will be understood that, although the terms first, second, etc. may be used herein to describe various elements, these elements or constituent elements should not be limited by these terms. These terms are only used to distinguish one element from another element. Thus, for example, a first element or a first component discussed below could be termed a second element or a second component without departing from the teachings of the present invention.

Unless defined otherwise, all terms (technical and scientific terms) used herein have the same meaning as commonly understood by one of ordinary skill in the art to which this invention belongs. Further, unless defined otherwise, all terms defined in generally used dictionaries may not be overly interpreted.

Hereinafter, a preferred embodiment of the present invention will be described with reference to the accompanying drawings. However, embodiments of the present invention may be modified to various forms, and the scope of the present invention is not limited to the embodiments described below. Moreover, the embodiments of the present invention are provided to more fully illustrate the invention to those having an average knowledge in the art. The shapes and sizes of the elements may be exaggerated for clarity in the drawings.

Hereinafter, a wearable device and a biometric authentication method thereof according to an embodiment of the present invention will be described.

FIG. 1 is a diagram illustrating a wearable device according to an embodiment of the present invention and a smart phone connected thereto.

Referring to FIG. 1, a wearable device 100 and a smart phone 110 according to an embodiment of the present invention communicate with each other using a short-range communication. The wearable device 100 has a shape that is wearable on a human body (e.g., an arm) using a band or the like, includes a motion sensor, generates the motion data by measuring the user's motion through the motion sensor, and performs the user's biometric authentication based on the motion data. Thus, a user may perform biometric authentication, only by walking while wearing the wearable device 100 without a separate operation. Since a movement pattern of an arm during walking differs depending on the walling pattern of each user, it is possible to perform the user's biometric authentication by measuring the movement of the arm.

Figure 2:
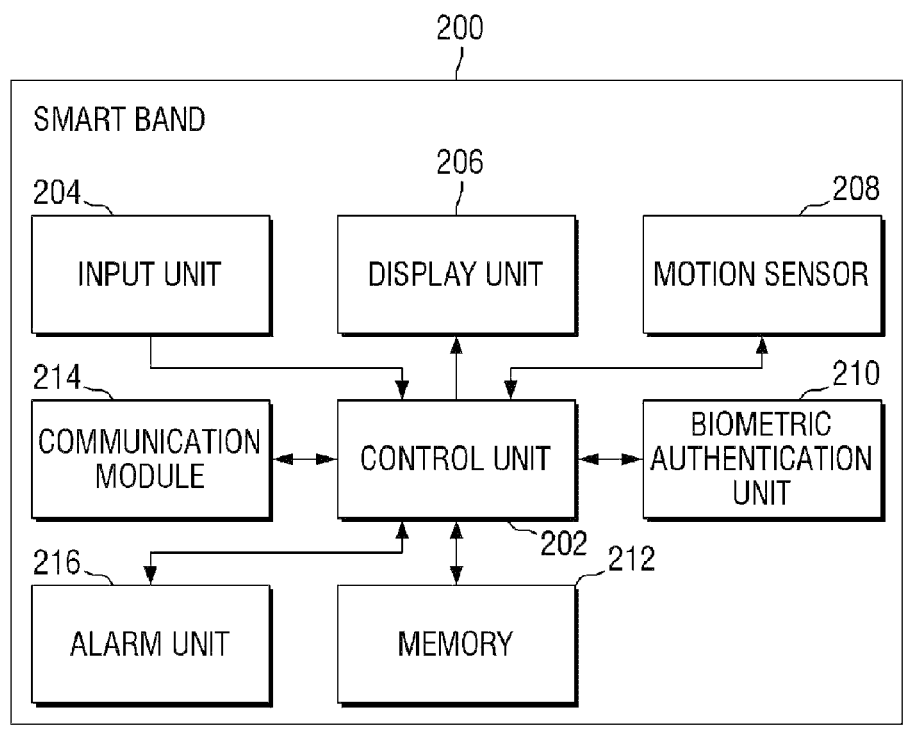
FIG. 2 is a block diagram illustrating a device configuration of the wearable device according to an embodiment of the present invention.

FIG. 2 is a block diagram illustrating a device configuration of a wearable device according to an embodiment of the present invention.

Referring to FIG. 2, a wearable device 200 according to an embodiment of the present invention includes a control unit 202, an input unit 204, a display unit 206, a motion sensor 208, a biometric authentication unit 210, a memory 212, a communication module 214 and an alarm unit 216.

The control unit 202 generates the motion data by measuring the user's motion through the motion sensor 208, and processes the functions for executing the user' biometric authentication base on the motion data.

The input unit 204 may be made up of a plurality of function keys, and provides key input data corresponding to keys pressed by a user to the controller 202. Here, the functions of the input unit 204 and the display unit 206 may be performed by a touch screen unit (not illustrated), and in this case, the touch screen unit (not illustrated) takes charge of the touch screen input through the user's screen touch and the graphic screen output through the touch screen.

The display unit 206 displays state information, a limited number of characters, a quantity of moving images and still images generated during the operation of the wearable device 200. The display unit 206 may use a liquid crystal display (LCD).

The motion sensor 208 is embodied as a sensor such as an acceleration sensor and a gyroscope, and is activated periodically or under the control of the biometric authentication unit 210 to measure the user's motion. Further, the motion sensor 208 generates the motion data including the measured result and provides the motion date to the biometric authentication unit 210.

When the necessity for the user's biometric authentication is determined, the biometric authentication unit 210 activates the motion sensor 208 to extract a plurality of feature points on the basis of the motion data generated by the motions sensor, and thereafter, the biometric authentication unit 210 performs the user's biometric authentication based on the distribution states of the extracted feature points. According to the embodiments, the biometric authentication unit 210 derives a histogram for the extracted feature points, and converts the derived histogram into a normalized histogram. Thereafter, biometric authentication unit 210 may check whether an error between the user's biometric authentication information registered in advance and the distribution state of the feature points within the normalized histogram is present within an allowable error range, by comparing the user's biometric authentication information registered in advance with the distribution state of the feature points within the normalized histogram. If an error between the user's biometric authentication information registered in advance and the distribution state of the feature points within the normalized histogram is present within an allowable error range, the biometric authentication unit 210 may determine that the normalized histogram is the same as the user's biometric authentication information registered in advance. If an error between the user's biometric authentication information registered in advance and the distribution state of the feature points within the normalized histogram are not present within an allowable error range, the biometric authentication unit 210 may determine that the normalized histogram is not the same as the user's biometric authentication information registered in advance.

The biometric authentication unit 210 registers the user's biometric authentication information for comparison with the normalized histogram in advance, in response to the registration request for the biometric authentication information before performing the user's biometric authentication. According to the embodiment, the biometric authentication unit 210 activates the motion sensor 208 in response to the registration request for the biometric authentication information through the user's key operation, extracts a plurality of feature points based on by the generated motion data, derives the histogram of the extracted feature points, and after converting the derived histogram into normalized histograms, the biometric authentication unit 210 may register the normalized histogram as the user' biometric authentication information.

The memory 212 stores microcode and various reference data of the program for processing and controlling the control unit 202, temporary data generated during execution of various programs, and various renewable storage data. In particular, the memory 212, stores the user's biometric authentication information registered in advance.

The communication module 214 encodes the signal input from the control unit 202, transmits the signal to a smart phone through a short-range wireless communication, such as Bluetooth, ZigBee, infrared, ultra wide band (UWB), wireless LAN (WLAN) and near field communication (NFC). Further, communication module 214 decodes the signal received from the smart phone through the short-range wireless communication and provides the signal to the control unit 202.

The alarm unit 216 reports the success/failure of the user's biometric authentication to a user under the control of the biometric authentication unit 210. Here, the alarm unit 216 may output an alarm so that a user recognizes the success/failure of the user's biometric authentication through the human sense, such as visual and auditory senses. For example, a warning sound may be output or a warning light may be flickered using a buzzer or a light emitting diode (LED), and an alarm may be output to report the success/failure of the biometric authentication, by the guide display through the display unit 206.

Figure 3:
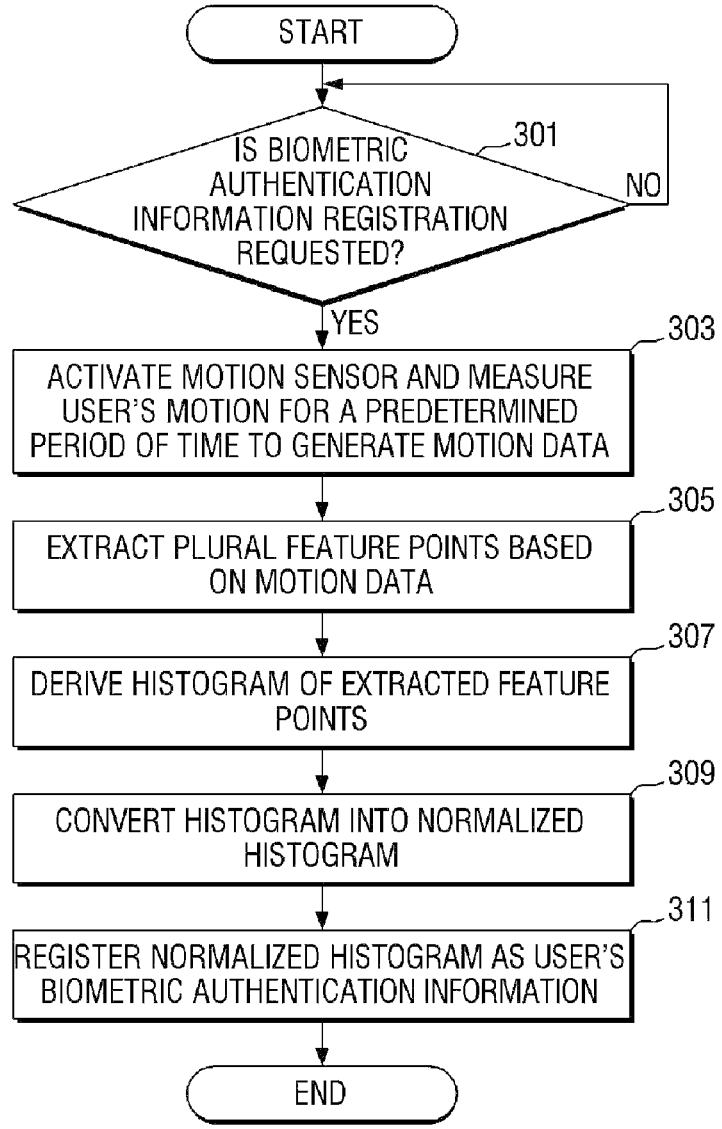
FIG. 3 is a flow chart illustrating a method of registering biometric authentication information in the wearable device according to an embodiment of the present invention.

FIG. 3 is a flow chart illustrating a method of registering the biometric authentication information in the wearable device according to an embodiment of the present invention.

Referring to FIG. 3, the wearable device checks whether the registration of biometric authentication information is requested depending on the user's key operation at step 301.

At step 301, when the registration of the biometric authentication information is requested depending on the user's key operation, the wearable device activates the motion sensor 208 at step 303, and generates the motion data by measuring the user's motion for a predetermined period of time. For example, when the motion sensor is an acceleration sensor, the wearable device generates the acceleration data by measuring the acceleration of the user's motion, and when the motion sensor is a gyroscope, the wearable device generates an angular velocity data by measuring a rotational angular velocity of the user's motion. Here, the acceleration data includes the three-axis (x, y and z-axis) acceleration components, and the angular velocity data includes the three-axis angular velocity components.

Thereafter, the wearable device extracts a plurality of feature points, based on the motion data generated in the motion during a predetermined period of time at step 305. For example, when the motion data is an acceleration data, the magnitude of the acceleration may become the feature point, and the magnitude of the acceleration may be calculated by taking the root of the result value that is added by squaring each of the three-axis acceleration components. Also, when the motion data is an angular velocity data, the magnitude of the rotational angular velocity may become the feature point, and the magnitude of the rotational angular velocity may be calculated by taking the root of the result value that is added by squaring each of the three-axis angular velocity components. Further, Fourier transformation execution results of the magnitude of the acceleration or the magnitude of the rotational angular velocity may become the feature points.

Thereafter, the wearable device derives the histogram of the extracted feature points at step 307. The histogram is a graph illustrating the distribution state of the extracted feature points.

Thereafter, the wearable device converts the derived histogram into the normalized histogram for easy comparison between the histograms when performing the future biometric authentication at step 309.

Thereafter, the wearable device registers the normalized histogram as user's biometric authentication information at step 311.

Thereafter, the wearable device finishes the algorithm according to the present invention.

Figure 4:
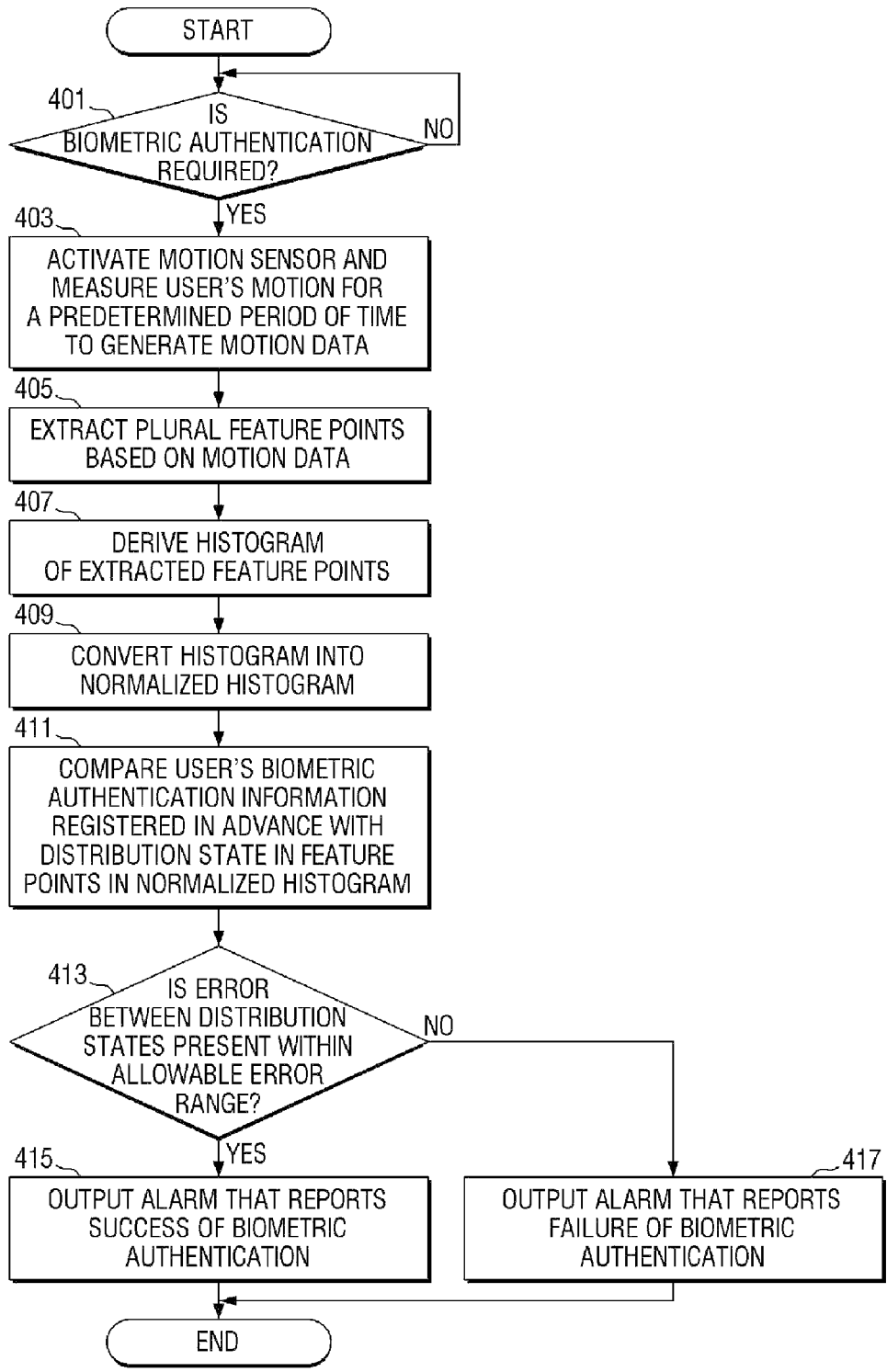
FIG. 4 is a flow chart illustrating a method for performing the biometric authentication based on the biometric authentication information registered in the wearable device according to an embodiment of the present invention.

FIG. 4 is a flow chart illustrating a method for performing a biometric authentication based on the biometric authentication information registered in the wearable device according to an embodiment of the present invention.

Referring to FIG. 4, the wearable device checks whether there is a need to periodically perform the user's biometric authentication at step 401.

At step 401, when it is determined that there is a need for user's biometric authentication, the smart band activates the motion sensor at step 403 and generates the motion data by measuring the user's motion for a predetermined period of time. For example, when the motion sensor is an acceleration sensor, it generates the acceleration data by measuring the acceleration of the user's motion, and when the motion sensor is a gyroscope, it generates the angular velocity data by measuring the rotational angular velocity of the user's motion. Here, the acceleration data includes the three-axis (x, y and z-axis) acceleration components, and the angular velocity data includes the three-axis angular velocity components.

Thereafter, the wearable device extracts a plurality of feature points, based on the motion data generated in the motion during the predetermined period of time at step 405. For example, when the motion data is an acceleration data, the magnitude of the acceleration may becomes the feature point, and the magnitude of the acceleration may be calculated by taking the root of the result value that is added by squaring each of the three-axis acceleration components. Also, when the motion data is an angular velocity data, the magnitude of the rotational angular velocity may become the feature point, and the magnitude of the rotational angular velocity may be calculated by taking the root of the result value that is added by squaring each of the three-axis angular velocity components. Further, the Fourier transformation execution results of the magnitude of the acceleration and the magnitude of the rotational angular velocity may become the feature points.

Next, the wearable device derives the histogram of the extracted feature points at step 407. The histogram is a graph illustrating the distribution state of the extracted feature points.

Next, the wearable device converts the derived histogram into a normalized histogram at step 409.

Next, the wearable device compares the user's biometric authentication information registered in advance with the distribution state of the feature points in the normalized histogram at step 411.

Next, the wearable device checks whether an error between the user's biometric authentication information registered in advance and the distribution state of the feature points in the normalized histogram is present within an allowable error range at step 413. For example, the wearable device finds a difference between the user's biometric authentication information registered in advance (i.e., the user's normalized histogram registered in advance) and each section in the normalized histogram, determines a score by taking and adding the absolute value, and determines whether the determined score is equal to or less than a reference value. Thus, the wearable device may check whether an error between the user's biometric authentication information registered in advance and the distribution state of the feature points in the normalized histogram is present within an allowable error range. Here, the lower the determined score is, the higher the similarity between the two normalized histograms is. According to the embodiment, the wearable device may comprise two or more motion sensors different from each other. In this case, the wearable device determines two or more scores on the basis of the motion data generated using two or more motion sensors, determines the final score by adding after applying the weight to each of the determined two or more scores, and by determining whether the determined final score is equal to or less than the reference value, the wearable device may determine whether the error between the user's biometric authentication information registered in advance and the distribution state of the feature points in the normalized histogram is present within an allowable error range.

When the error between the user's biometric authentication information registered in advance and the distribution state of the feature points in the normalized histogram is present within an allowable error range at step 413, the wearable device determines that the normalized histogram is the same as the user's biometric authentication information registered in advance at step 415, and outputs an alarm that reports a success of the biometric authentication to a user.

Meanwhile, when the error between the user's biometric authentication information registered in advance and the distribution state of the feature points in the normalized histogram is not present within the allowable error range at step 413, the wearable devices determines that the normalized histogram is not the same as the user's biometric authentication information registered in advance at step 417, and outputs an alarm that reports a failure of the biometric authentication to a user.

Next, the wearable device finishes the algorithm according to the present invention.

The wearable device equipped with the acceleration sensor according to an embodiment of the present invention may perform the user's biometric authentication by extracting the magnitude of acceleration as the feature points.

As long as a user simply walks without a separate operation after wearing the wearable device equipped with an acceleration sensor, the wearable device generates the acceleration data by measuring the acceleration of the user's motion and may extract a plurality of feature points by calculating the magnitude of the acceleration based on the acceleration data. Next, the wearable device derives the histogram of the extracted feature points and converts the derived histogram into the normalized histogram. Thereafter, the wearable device may perform the user's authentication by comparing the user's biometric authentication information registered in advance (i.e., the normalized histogram registered in advance) with the normalized histogram.

The wearable device equipped with the gyroscope according to an embodiment of the present invention may perform the user's biometric authentication, by extracting the magnitude of rotational angular velocity size as the feature points.

As long as a user simply walks without a separate operation after wearing the wearable device equipped with a gyroscope, the wearable device may generate the angular velocity data by measuring the rotational angular velocity of the user's motion and may extract a plurality of feature points by calculating the magnitude of the rotational angular velocity based on the data. Next, the wearable device derives the histogram of the extracted feature points and converts the derived histogram into the normalized histogram. Thereafter, the wearable device may perform the user's authentication by comparing the user's biometric authentication information registered in advance (i.e., the user's normalized histogram registered in advance) with the normalized histogram.

The wearable device equipped with an acceleration sensor or a gyroscope according to an embodiment of the present invention may perform the user's biometric authentication, by extracting the Fourier transformation execution results of the magnitude of the acceleration or the magnitude of the rotational angular velocity as the feature points.

As long as a user simply walks without a separate operation after wearing the wearable device equipped with an acceleration sensor or a gyroscope, the wearable device generates the acceleration data or the angular velocity data by measuring the acceleration or the rotational angular velocity of the user's motions, and calculates the magnitude of the acceleration and the magnitude of the rotational angular velocity based on the data. Thereafter, the wearable device may extract a plurality of feature points by performing the Fourier transformation. Thereafter, the wearable device derives the histogram of the extracted feature points, and converts the derived histogram into the normalized histogram. Thereafter, the wearable device may perform the user's authentication, by comparing the user's biometric authentication information registered in advance (i.e., the user's normalized histogram registered in advance) with the normalized histogram.

Thus, the wearable device and the method for biometrics authentication thereof according to an embodiment of the present invention have an advantage capable of performing the biometric authentication by simply walking while wearing a wearable device without an additional circuit and a separate operation, by measuring the user's motion using the motion sensor to generate the motion data, and by performing the user's biometric authentication based on the data.

Hereinafter, each score of the first to third elements determined by the control unit will be described with reference to FIGS. 5 to 8.

FIGS. 5 to 8 are diagrams illustrating each score of the first to third elements determined by the control unit of FIG. 2.

Figure 5:
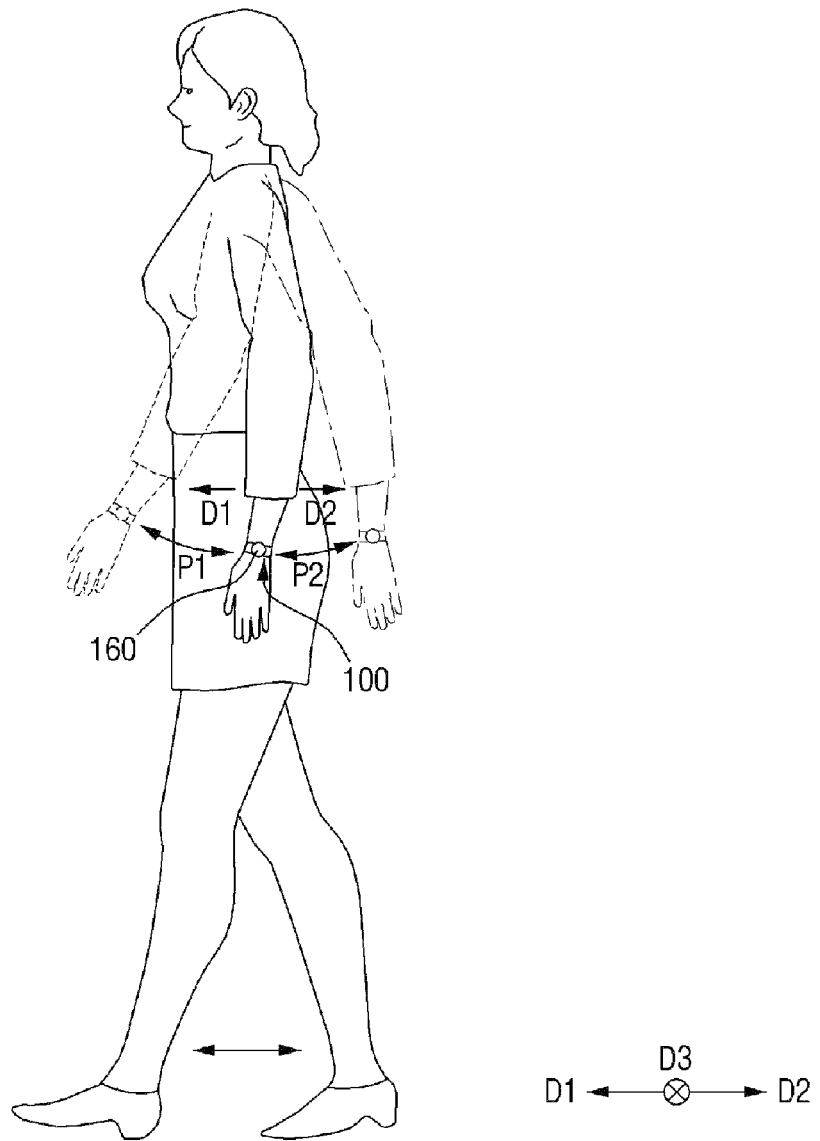
FIGS. 5 to 8 are diagrams illustrating scores of each of the first to third elements determined by a control unit of FIG. 2.
Figure 6:
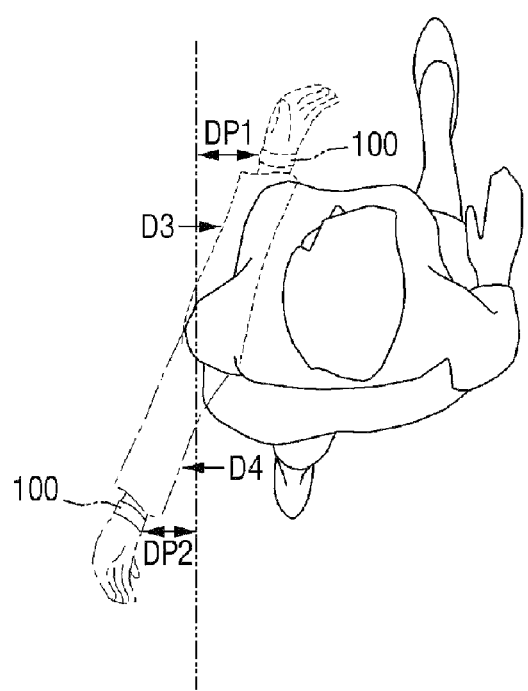

First, FIGS. 5 and 6 illustrate figures in which a user swings arms back and forth during walking. That is, in general, when a person naturally wings arms back and forth (in a walking direction) during walking, and at this time, the angle of swinging the arms back and forth may differ from person to person. Moreover, as the time taken for walking one step is long (that is, as the stride is relatively large), a human body may be adversely affected.

A first element serving as criteria of the user's motion state is exactly based on this point. That is, the score of the first element may be determined on the basis of a first movement time and a second movement time. The first movement time is up to a first peak angle P1 in a first direction D1 of directions in which a user swings arms during walking based on a state S1 in which the user's arms are positioned parallel to the user's body, and a second movement time is up to a second peak angle P2 in a second direction D2 opposite to the first direction D1.

More specifically, after extracting the values obtained by integrating the rotational angular velocity components in a third direction D3 (e.g., a direction perpendicular to a liquid crystal surface of the display unit 160 of the smart band 100) intersecting with the first and second directions D1 and D2 (i.e., the first peak angle P1 in the first direction D1 and the second peak angle P2 in the second direction D2 with respect to the directions (first and second directions D2) of swinging the arms back and forth), the score of the first element may be determined, based on the movement time between the first peak angle P1 and the second peak angle P2. In the case of the present invention, since the noise may occur when integrating the acceleration components or the rotational angular velocity components, it is possible to use a filter to remove noise.

The formula for calculating the score of the first element, for example, may be <Formula 1>.

Score of first element=(10000−(average of first movement time+average of second movement time)/2)²/100)    <Formula 1>

Here, the first movement time and the second movement time may be measured multiple times, and the average of the first movement time and the average of second movement time may be determined by extracting the data corresponding to the specific ranges (e.g., 90 to 110% of the average range) of the first movement time and the second movement time measured multiple times, but it is not limited thereto.

Thus, the score of the first element may be determined based on the rotational angular velocity of the user's motion, and the larger the sum of the first and second movement times is, the smaller the score of the first element may be.

Next, FIG. 6 illustrates a figure in which a user swings arms inside and outside during walking. That is, in general, a person swings arms inside and outside (i.e., inside and outside of the body) during walking, and at this time, the angle in which the person swings arms inside and outside) may differ from person to person. In addition, in many cases, the larger the width of moving the arm inside and outside is, the more the rotation of the body is. In many cases, the more the rotation of the body is, the more the adverse effect on the pelvis is.

A second element serving as criterion of a user's motion state is exactly based on this point. That is, the score of the second element may be determined based on the first peak displacement DP1 in the third direction D3 and the second peak displacement DP2 in the fourth direction D4 opposite to the third direction D3, in the directions that a user swings arms based on the state (S1 in FIG. 3) in which the user's arms are positioned in parallel with the user's body.

More specifically, after extracting the values obtained by integrating the acceleration components in the third direction D3 (e.g., a direction perpendicular to a liquid crystal surface of the display unit (160 in FIG. 3) of the smart band (100 in FIG. 3)) (i.e., the first peak displacement DP1 in the third direction D3 and the second peak displacement DP2 in the fourth direction D3 with respect to the directions (third and fourth directions D2) of swinging the arms inside and outside).

The formula for calculating the score of the second element, for example, may be <Formula 2>.

Score of second element=(50/((average of first peak displacement+average of second peak displacement)/2)*10))    <Formula 2>

Here, the first peak displacement DP1 and the second peak displacement DP2 may be measured multiple times, and the score of the second element may be determined on the basis of the average of the first peak displacement DP1 and the second peak displacement DP2 measured multiple times.

Thus, the score of the second element may be determined based on the acceleration of the user's motion, and the larger the sum of the first and second peak displacement is, the smaller the core of the second element may be.

Figure 7:
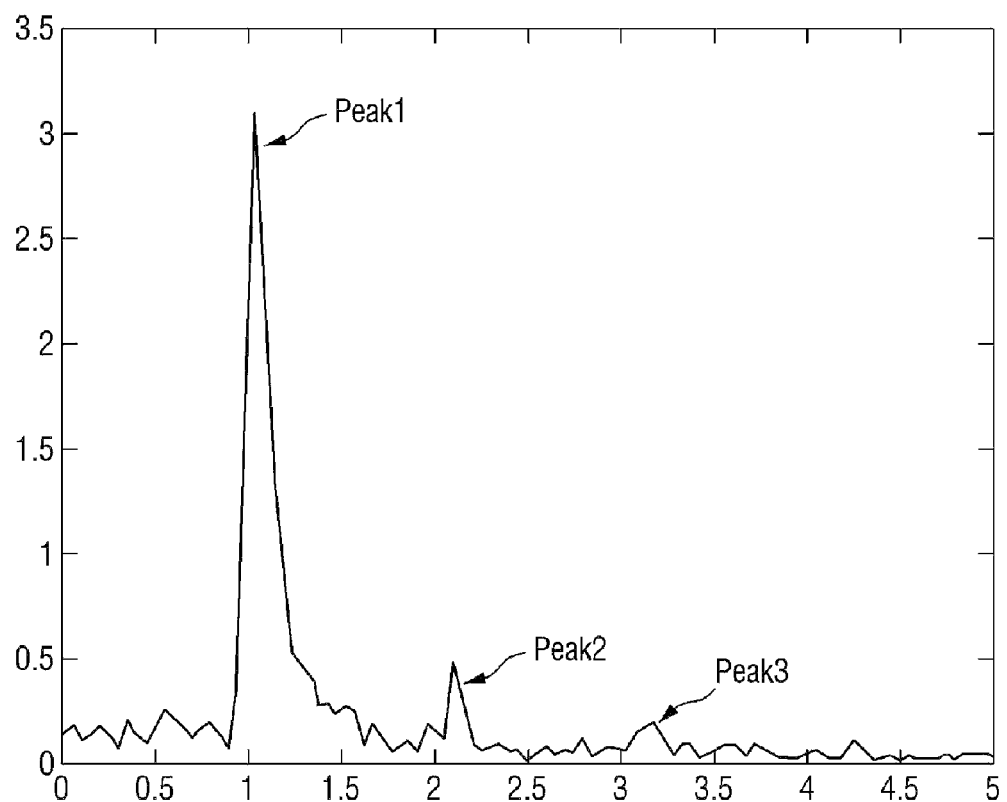
Figure 8:
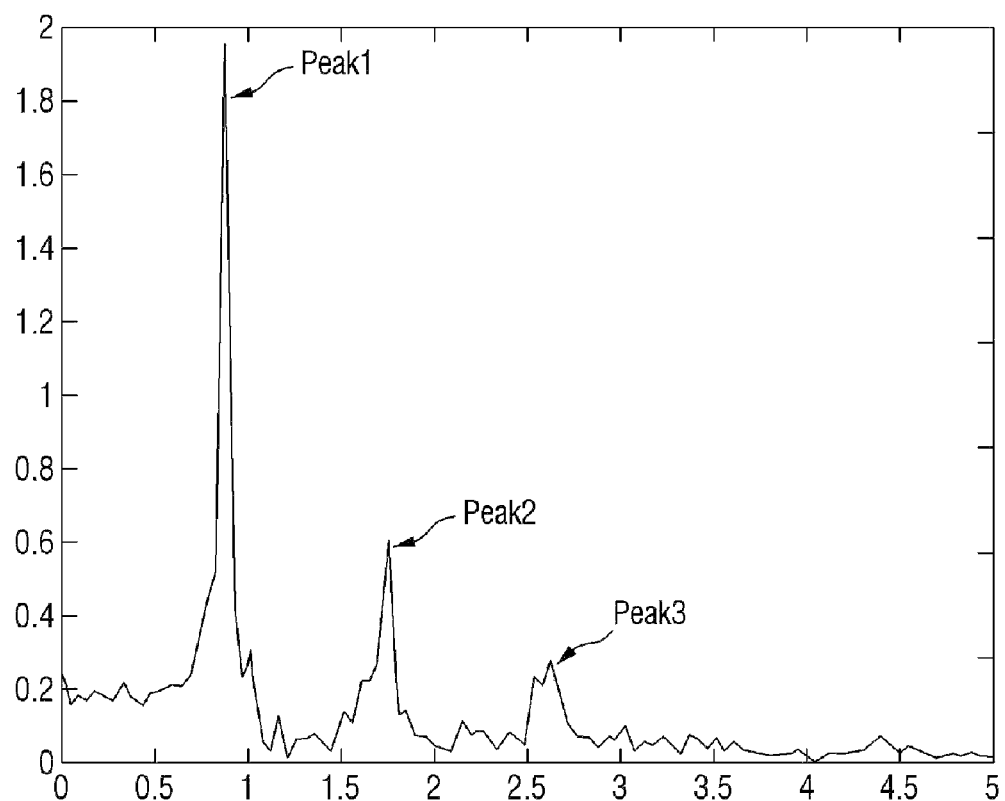

Next, referring to FIGS. 7 and 8, it is possible to know whether the user's walking is periodical or gives an impact on the feet, through the frequency analysis of the integral value of the rotational angular velocity of the user's motion.

Specifically, FIGS. 7 and 8 are graphs obtained by performing the Fourier transformation of the integral values of the rotational angular velocity components in the third direction (D3 in FIG. 3) (e.g., a direction perpendicular to the liquid crystal surface of the display unit 160 of the smart band 100) which intersects with the first and second directions (D1 and D2 in FIG. 3) described in FIG. 5.

First, in the case of FIG. 7, this is a graph in the case of good walking, and it is possible to know that remaining peaks (e.g., the second peak Peak 2 and the third peak Peak 3) are smaller than the first peak Peak1.

In contrast, in the case of FIG. 8, this is a graph in the case of bad walking, and it is possible to know that that remaining peaks (e.g., the second peak Peak 2 and the third Peak 3) are greater than the first peak Peak 1 as compared to FIG. 7.

That is, when other peaks are present in addition to the main peak (i.e., the first peak Peak1), or when other present peaks are large, this may be called walking containing many noise, i.e., walking that is not periodic and gives an impact on the feet.

Thus, a third element serving as criterion for the user's motion condition is exactly based on this point. That is, the score of the third element may be determined, based on the sum of the magnitudes of the remaining peaks (e.g., second and third peak Peak 3) in comparison to the magnitude of the first peak (i.e., first peak Peak 1) of the frequency region of the integral value of the rotational angular velocity, after performing the Fourier transformation of the values by integrating the rotational angular velocity components in the third direction D3 of FIG. 3.

Here, a proportion of (the magnitude of the first peak:sum of the magnitudes of the second and third peaks) may be calculated using a particular function (e.g., WalkMeterCalc).

The formula for calculating the score of the third element, for example, may be <Formula 3>.

Score of third element=100−(WalkMeterCalc(gyro (2,;))*50)    <Formula 3>

Here, the remaining peaks are not limited to the second and third peaks, and may comprise additional peaks in addition to the second and third peaks.

Thus, the score of the third element may be determined based on the rotational angular velocity of the user's motion, and the greater the sum of the magnitudes of the remaining peaks except the first peak is, the smaller the score of the third element may be.

In summary, the final score is calculated in the control unit (202 in FIG. 2) based on the scores of each of the first to third elements calculated in the manner described above, and the control unit (202 in FIG. 2) may determine the user's motion state by comparing the final score to the user's normal motion score stored in the memory (212 in FIG. 2).

Here, the formula for calculating the final score, for example, may be <Formula 4>.

Final score=score of first element*score of second element*score of third element/10000  <Formula 4>

Also, the user's normal motion score, for example, may be a score of a specific range rather than a specific score, when the final score is higher than the user's normal motion score, it may be the good walking, and when the final score is lower than the user's normal motion score, it may be the bad walking.

Also, the alarm unit (216 in FIG. 2) described above may output an alarm to the user, when the final score is lower than the normal motion score.

The smart band 100 according to an embodiment of the present invention analyzes a degree of healthy of the user's walking through the motion sensor 208 and the control unit 202, and when the final score is lower than the user's normal motion score, the smart band may provide an alarm in real time. Moreover, the smart band 100 may assist the user to maintain a healthy walking by providing an alarm in real time in this manner.

The motion operation determination method of the smart band will be described below with reference to FIGS. 9 and 10.

Figure 9:
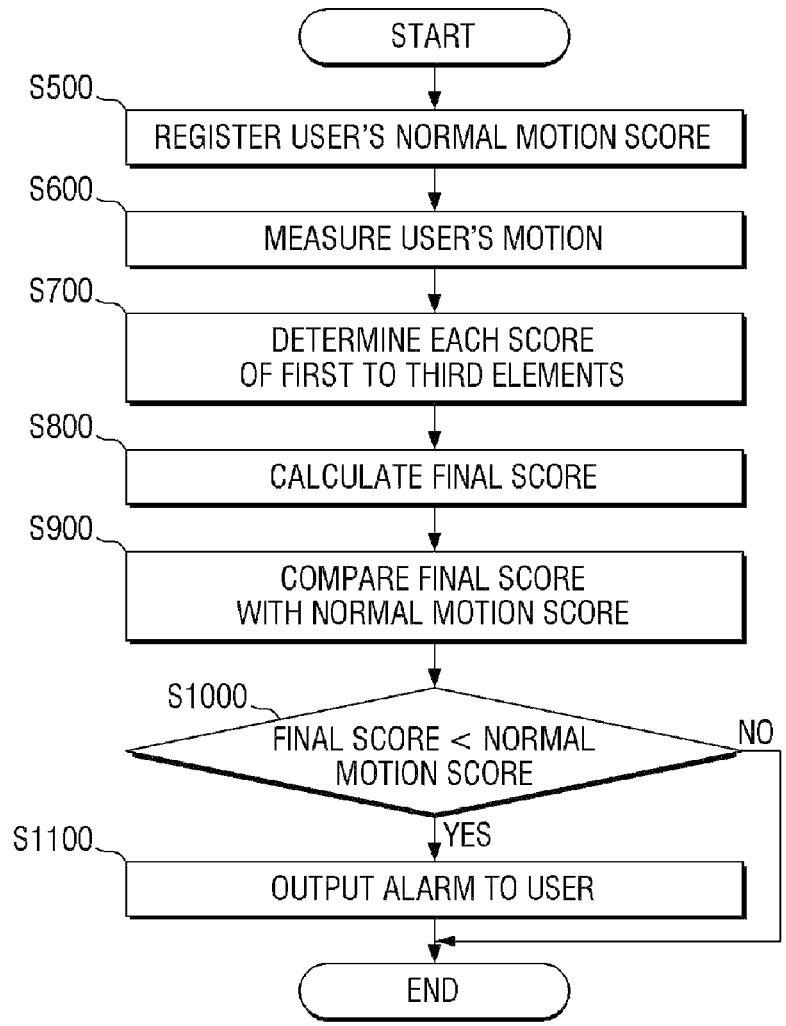
FIG. 9 is a flow chart illustrating the motion operation determination method of a smart band according to an embodiment of the present invention.

FIG. 9 is a flow chart illustrating the motion operation determination method of the smart band according to an embodiment of the present invention. FIG. 10 is a flow chart illustrating a registration procedure of the user's normal motion score of FIG. 9.

Referring to FIG. 9, first, the user's normal motion score is registered (S500).

Figure 10:
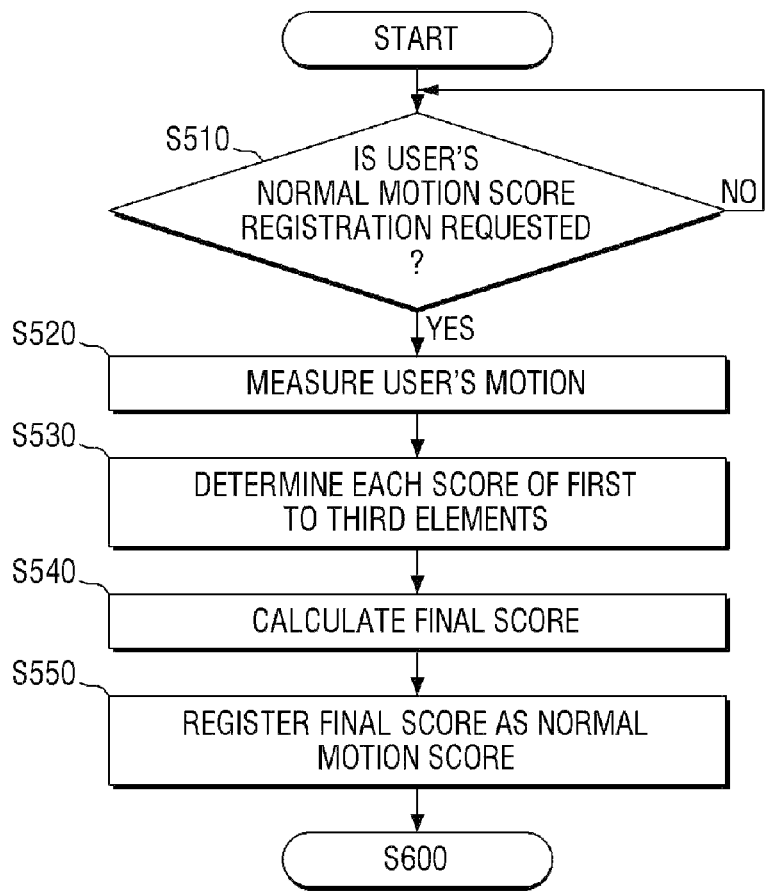
FIG. 10 is a flow chart illustrating the user's normal motion score registration procedure of FIG. 9.

Specifically, referring to FIGS. 2 and 10, when the registration of the normal motion score is requested depending on the user's key operation (S110), the smart band 100 activates the motion sensor 208, and generates the motion data by measuring the user's motion for a predetermined period of time (S520). For example, when the motion sensor 208 is an acceleration sensor, it generates the acceleration data by measuring the acceleration of the user's motion, and when the motion sensor 208 is a gyroscope, it generates the angular velocity data by measuring the rotational angular velocity of the user's motion. Here, the acceleration data includes the three-axis (x, y and z-axis) acceleration components, and the angular velocity data includes the three-axis angular velocity components.

Next, the scores of each of the first to third elements are determined on the basis of the motion data generated in the motion for a predetermined period of time (S530).

Specifically, the determination of the score of the first element may comprise the multiple measurements of a first movement time and a second movement time, and the determination of the score of the first element based on the average of each of the first and second movement times measured multiple times. The first movement time is up to a first peak angle (P1 in FIG. 5) in a first direction (D1 in FIG. 5) and the second movement time is up to a second peak angle (P2 in FIG. 5) in a second direction (D2 in FIG. 5) opposite to the first direction (D1 in FIG. 5), among the directions in which a user swings arms based on the state (S1 in FIG. 5) in which the user's arms are positioned parallel to the user's body.

Furthermore, the determination of the score of the second element may comprise measurement of a first peak displacement (DP1 in FIG. 6) and a second peak displacement (DP2 in FIG. 6) in multiple times, and the determination of the score of the second element based on the average of each of the first and second peak displacements (DP1 and DP2 in FIG. 6) measured multiple times. The first peak displacement is performed in the third direction (D3 in FIG. 6) intersecting with the first direction (S1 in FIG. 6) and the second peak displacement (DP2 in FIG. 6) is performed in the fourth direction (D4 in FIG. 6) opposite to the third direction (D3 in FIG. 6), among the directions in which a user swings arms based on the state (S1 in FIG. 5) in which the user's arms are positioned parallel to the body.

The determination of the score of the third element may comprise conversion of the integral value of the rotational angular velocity of the user's motion into the frequency region through the Fourier transformation, and determination of the score of the third element based on the proportion of the sum of the magnitudes of the remaining peaks in comparison to the magnitude of the first peak in the frequency region of the integral value of the rotational angular velocity.

Next, the final score is calculated (S540).

Specifically, the control unit 202 may calculate the final score, by adding up the respective scores of the first to third elements.

Finally, the final score is registered as a normal motion score (S550). Specifically, the control unit 202 may register the calculated final score as a user's normal motion score and may store it in the memory 212.

Referring to FIGS. 2 and 9 again, the user's motion is measured (S600). Specifically, after the user's normal motion score is registered (S500), the motion sensor 208 is activated periodically or under the control of control unit 202, and it is possible to generate motion data by measuring the user's motion for a predetermined period of time. For example, when the motion sensor 208 is an acceleration sensor, it generates the acceleration data by measuring the acceleration of the user's motion, and when the motion sensor 208 is a gyroscope, it generates the angular velocity data by measuring the rotational angular velocity of the user's motion. Here, the acceleration data includes the three-axis (x, y and z-axis) acceleration components, and the angular velocity data includes the three-axis angular velocity components.

Next, the scores of each of the first to third elements are determined on the basis of the motion data generated in the motion for a predetermined period of time (S700).

Specifically, the determination of the score of the first element may comprise the multiple measurements of a first movement time and a second movement time, and determination of the score of the first element based on the average of each of the first and second movement times measured multiple times. The first movement time is up to a first peak angle (P1 in FIG. 5) in a first direction (D1 in FIG. 5) and the second peak angle (P2 in FIG. 5) is in a second direction (D2 in FIG. 5) opposite to the first direction (D1 in FIG. 5), among the directions in which a user swings arms based on the state (S1 in FIG. 5) in which the user's arms are positioned parallel to the body.

Furthermore, the determination of the score of the second element may comprise multiple measurements of the first peak displacement (DP1 in FIG. 6) and the second peak displacement (DP2 in FIG. 6), and determination of the score of the second element based on the average of each of the first and second peak displacements (DP1 and DP2 in FIG. 6) measured multiple times. The first peak displacement is in the third direction (D3 in FIG. 6) intersecting with the first direction (S1 in FIG. 6), and the second peak displacement is in the fourth direction (D4 in FIG. 6) opposite to the third direction (D3 in FIG. 6), among the directions in which a user swings arms based on the state (S1 in FIG. 5) in which the user's arms are positioned parallel to the body.

The determination of the score of the third element may comprise conversion of the integral value of the rotational angular velocity of the user's motion into the frequency region through the Fourier transformation, and determination of the score of the third element based on the proportion of the sum of the magnitudes of the remaining peaks in comparison to the magnitude of the first peak in the frequency region of the integral value of the rotational angular velocity.

Next, the final score is calculated (S800).

Specifically, the control unit 202 may calculate the final score, by adding up the respective scores of the first to third elements.

The final score is compared to the normal motion score (S900).

Specifically, the control unit 202 may determine whether the final score is smaller than the normal motion score by comparing the final score with the normal motion score stored in the memory 212 (S1000).

If the final score is smaller than the normal motion score, the control unit 202 sends a signal to the alarm unit 216, and the alarm unit 216 outputs an alarm to the user (S1100). Also, when the final score is greater than or equal to the normal motion score, the control unit 202 may not send a signal to the alarm unit 216, but it is not limited thereto. That is, even when the final score is greater than or equal to the normal motion score, the control unit 202 may send a signal to the alarm unit 216, and thus, the alarm unit 216 may output the alarm to a user. Of course, in this case, when the final score is smaller than or equal to or greater than the normal motion score, the alarm unit 216 may differently output the alarm to the user.

Thereafter, the smart band 100 finishes the algorithm according to an embodiment of the present invention.

The motion state determination method of the smart band according to the embodiments of the present invention may be embodied as a computer-readable code or program in a computer-readable recording medium. The computer-readable recording medium includes all kinds of recording devices that store data readable by a computer system. That is, the computer-readable recording medium may comprise program commands, data files, data structures and the like alone or in combination. The program commands recorded in the recording medium may be specifically designed and constructed for the present invention and may be known and available to a person having ordinary skill in the computer software art. Examples of computer-readable recording medium are a ROM, a RAM, a CD-ROM, a magnetic tape, a floppy disk, an optical data storage device and the like, and also include those embodied in the form of carrier waves (e.g., data transmission through Internet). Also, the computer-readable recording medium may be distributed to a computer system connected to a network, and the computer-readable code may be executed in a distributed manner.

Figure 11:
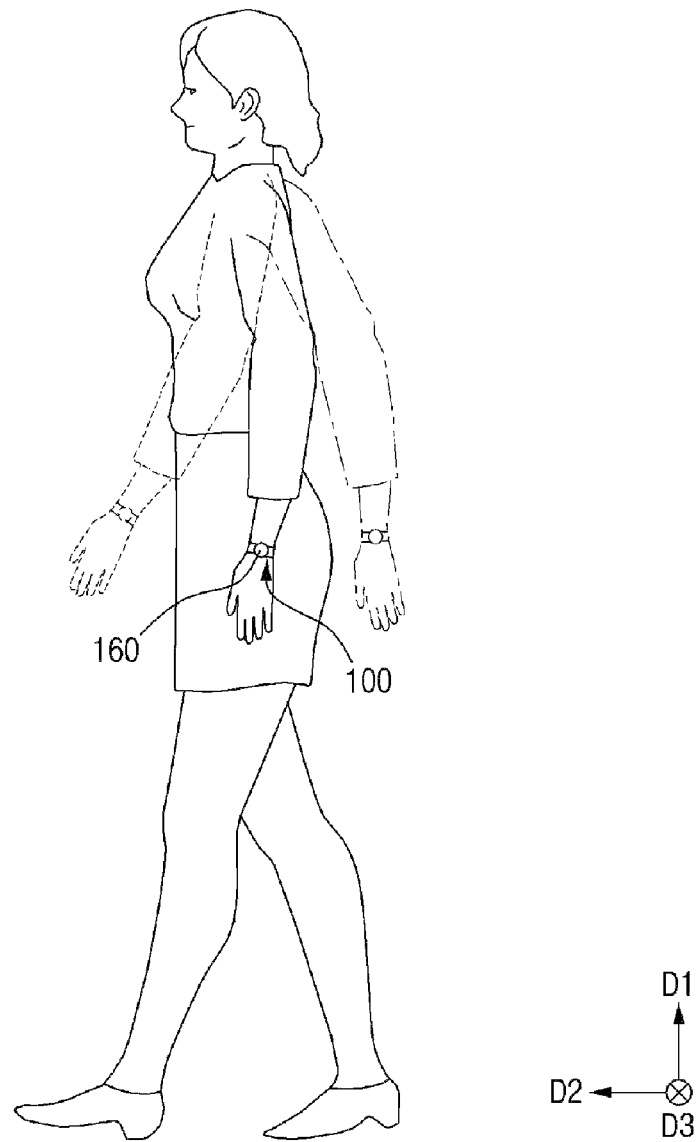
FIG. 11 is a diagram illustrating a state in which a user moves while wearing a smart band of FIG. 2.

Referring to FIG. 11, directional axes D1 and D2 of each of the integral values of the first and second rotational angular velocities intersect with each other and are positioned on the same plane as the liquid crystal surface of the display unit 160. The directional axis D3 of the integral value of the third rotational angular velocity may intersect with the respective directional axes D1 and D2 of the integral values of the first and second rotational angular velocities and may be perpendicular to the liquid crystal surface of the display unit 160.

Additionally, the rotation matrix, for example, may be <Formula 1>.

<Formula 1> rotationmatrix=[cos(yaw(i))*cos(roll(i))cos(yaw(i))
*sin(roll(i))*sin(pitch(i))sin(yaw(i))*cos(pitch(i))
cos(yaw(i))*sin(roll(i))*cos(pitch(i))+sin(yaw(i))
*sin(pitch(i)); sin(yaw(i))*cos(roll(i))sin(yaw(i))
*sin(roll(i))*sin(pitch(i))+cos(yaw(i))*cos(pitch
(i))sin(yaw(i))*sin(roll(i))*cos(pitch(i))−cos(yaw
(i))*sin(pitch(i)); −sin(roll(i))cos(roll(i))*sin
(pitch(i))cos(roll(i))*cos(pitch(i))];

Here, the integral value of the first rotating angular velocity may be a pitch (i), the integral value of the second rotating angular velocity may be a roll (i), and the integral value of the third rotational angular velocity may be a yaw (i).

Referring to FIG. 2 again, the control unit 202 may comprise a filter (not illustrated) that filters the noise of the integral values of the first to third rotational angular velocities. The filter (not illustrated) may filter the noise of the rotational angular velocity measured by the gyroscope before the correction, and for example, may be a notch filter, but it is not limited thereto.

The control unit 202 calculates the linear acceleration by applying the rotation matrix to acceleration measured by the acceleration sensor (not illustrated), calculates the values of the velocity and displacement by integrating the linear acceleration, performs Fourier transformation of the integral value of the third rotational angular velocity, and may extract the second balance element based on the values of the velocity and displacement and the integral value of the third rotational angular velocity subjected to Fourier transformation.

The control unit 202 receives the supply of the first balance element from the memory 212, calculates the asymmetry index based on the difference between the first balance element and the second balance element, calculates the spinal score, the shoulder score and the pelvic score based on the asymmetry index, and may calculate the final score based on the spinal score, the shoulder score and the pelvic score.

Here, each of the first and second balance elements may comprise a plurality of sub-balance elements.

The plurality of sub-balance elements, for example, may comprise, but not limited to, a positive peak (a peak point when a user swings arms forward) of the integral value of the third rotational angular velocity, a negative peak (a peak point when a user swings arms backward) of the integral value of the third rotational angular velocity, positive and negative peaks (i.e., positive and negative peak points in the first direction D1 when a user swings arms) in the first direction D1 of FIG. 11, positive and negative peaks (i.e., positive and negative peak points in the second direction D2 when a user swings arms) in the second direction D2 of FIG. 11, positive and negative peaks (i.e., positive and negative peak points in the third direction D2 when a user swings arms) in the third direction D3 of FIG. 11, arm's movement time (arm's movement time up to the peak point when the user wings the arms forward in the attention attitude) up to the positive peak of the integral value of the third rotational angular velocity, and arm's movement time (arm's movement time up to the peak point when the user wings the arms backward in the attention attitude) up to the negative peak of the integral value of the third rotational angular velocity.

The formula for calculating the asymmetry index, for example, may be <Formula 2>.

Asymmetry index=100*(second balance element−1 balance elements)/second balance element   <Formula 2>

Here, the first balance element may be a balance element of the right arm's motion, and the second balance element may be a balance element of the left arm's motion, but are not limited thereto. In addition, one sub-balance elements of the second balance element may be substituted to <Formula 2>, and the sub-balance element of the first balance element corresponding thereto may be substituted.

If the first balance element is a balance element of the right arm's motion and the second balance element is a balance element of the left arm's motion, if the asymmetry index is greater than 0, it means that the left arm's motion is large.

Additionally, the control unit 202 may calculate the final asymmetry index by combining each asymmetry index, after calculating the asymmetry index of each sub-balance element.

Formula for calculating the final asymmetry index, for example, may be <Formula 3>.

Final asymmetry index=60+(0.5−(combination of each asymmetry index))*100     <Formula 3>

The control unit 1202 may calculate the spinal score, the shoulder score and the pelvic score based on the asymmetry index as described above, and the formula for calculating it is <Formulas 4, 5 and 6>.

Spine score={50+(0.2−(asymmetry index of positive peak of integral value of third rotational angular velocity+asymmetry index of negative peak of integral value of third rotational angular velocity))*200+25+(0.2−(asymmetry index of positive peak in second direction D2 of FIG. 11+asymmetry index of negative peak in second direction D2 of FIG. 11))*100}/1.5     <Formula 4>

Shoulder score=50+(0.2−(asymmetry index of positive peak in first direction D1 of FIG. 11+asymmetry index of negative peak in first direction D1 of FIG. 11))*200     <Formula 5>

Pelvis score={50+(0.2−(asymmetry index of positive peak in third direction D3 of FIG. 11+asymmetry index of negative peak in third direction D3 of FIG. 11))*200+25+(0.2−(asymmetry index of positive peak in second direction D2 of FIG. 11+asymmetry index of negative peak in second direction D2 of FIG. 11))*100}/1.5     <Formula 6>

Furthermore, the final score may be calculated based on the spinal score, the shoulder score and the pelvic score that are assigned with specific weighted values, respectively.

The input unit 204 may receive the input from a user.

Specifically, the input unit 204 may be made up of a plurality of function keys, and provides the key input data corresponding to keys pressed by the user to the control unit 202. Here, the function of the input unit 204 and the display unit 160 may be performed by a touch screen unit (not illustrated), and in this case, the touch screen unit (not illustrated) is in charge of the touch screen input through the user's screen touch and the graphic screen output through the touch screen.

The display unit 160 may receive the supply of the output of the control unit 202 and display the output.

Specifically, the display unit 160 displays state information, a limited number of characters, a quantity of moving images and still images generated during the operation of the smart band 100. Further, the display unit 206 may comprise, for example, a liquid crystal display (LCD).

The communication module 214 may communicate with the peripheral electronic devices (e.g., a smart phone) by receiving the input signal from the control unit 202.

Specifically, the communication module 214 encodes the signal input from the control unit 202 and transmits the signal to the peripheral electronic devices (e.g., a smart phone) through a short-range wireless communication, such as Bluetooth, ZigBee, infrared, Ultra Wide Band (UWB), wireless LAN (WLAN) and Near Field Communication (NFC). Further, the communication module decodes the signal received from the peripheral electronic devices through the short-range wireless communication and provides the signal to the control unit 202.

The smart band 100 according to an embodiment of the present invention may provide the body balance, i.e., asymmetric information of a body type, by measuring the motion of user's both arms through the motion sensor 208 and the control unit 202. Moreover, the smart band 100 may assist the user to maintain the healthy body balance, by providing the user's body balance to the user.

The method for measuring the body balance of the smart band will be described below with reference to FIGS. 12 and 14.

Figure 12:
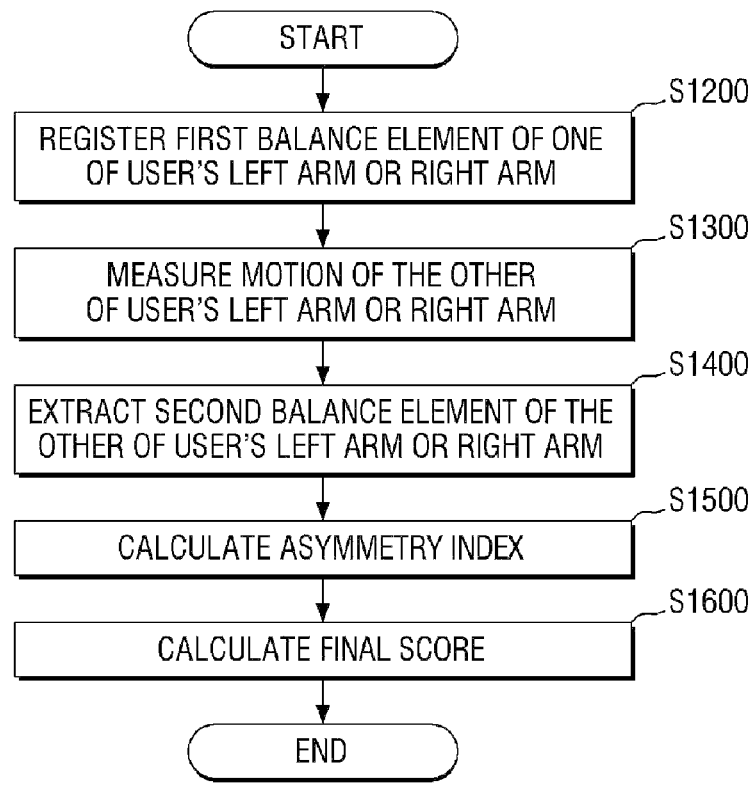
FIGS. 12 and 14 are flow charts illustrating a method for measuring the body balance of the smart band according to an embodiment of the present invention.
Figure 13:
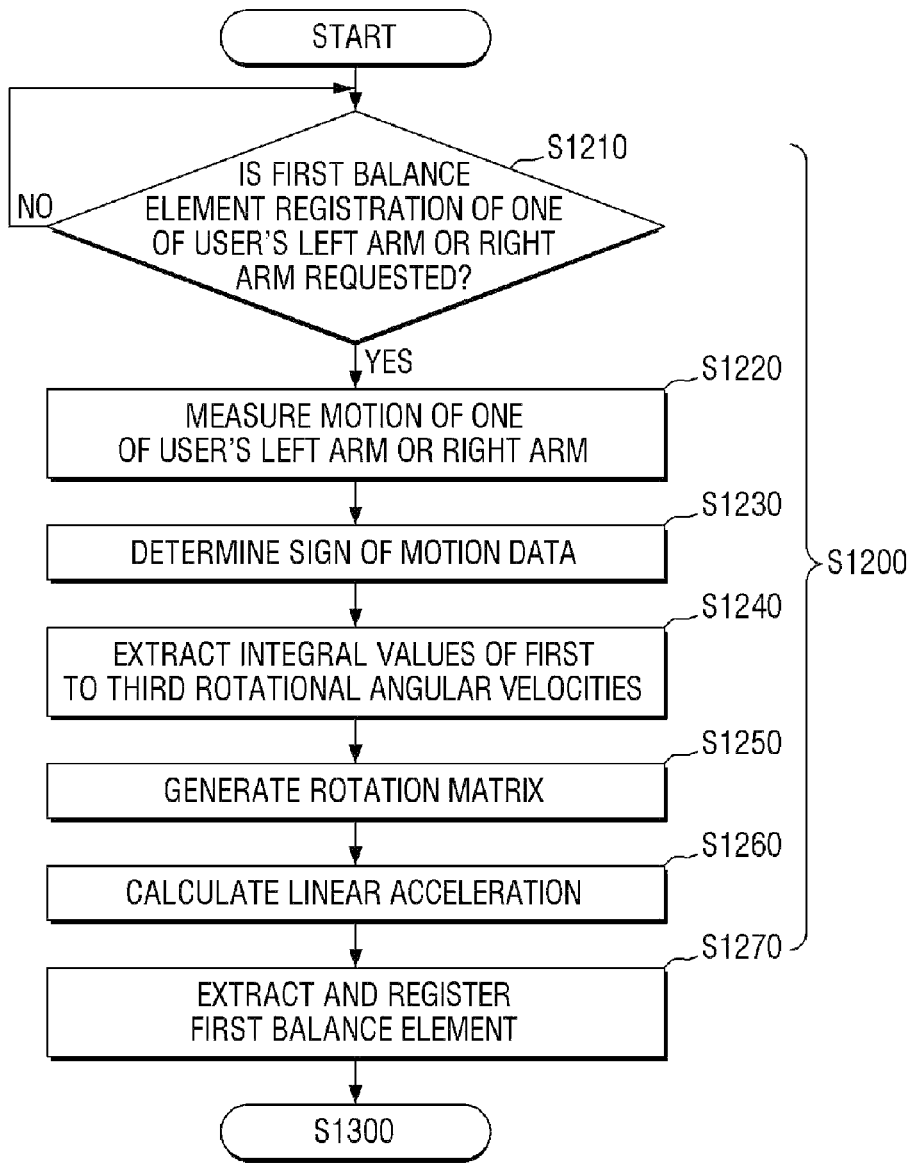
Figure 14:
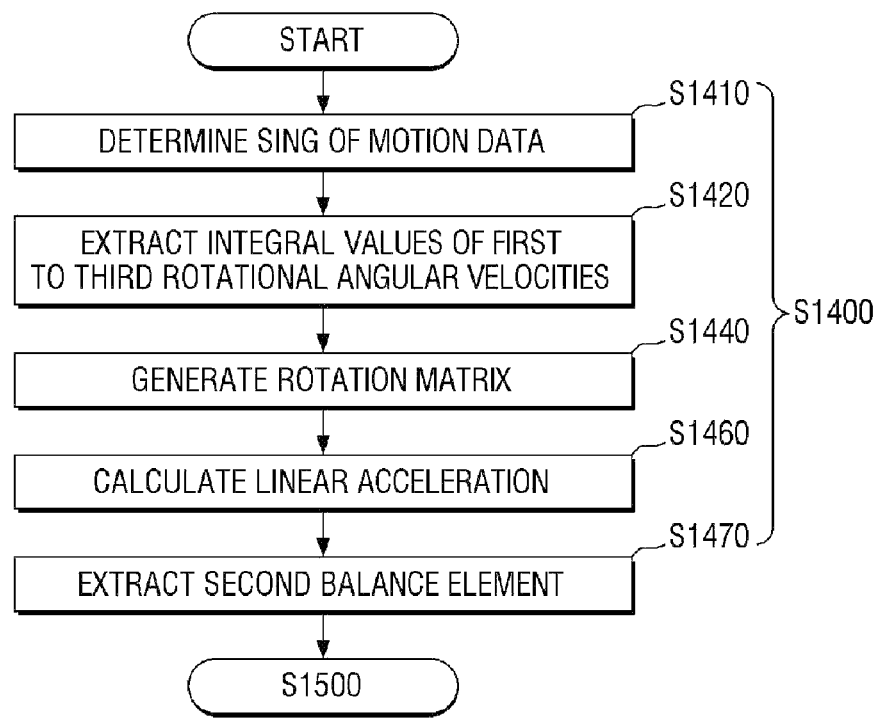

FIGS. 12 to 14 are flow charts illustrating the method for measuring the body balance of the smart band according to an embodiment of the present invention.

Referring to FIG. 1, the first balance element of one (e.g., a right arm) of the user's left arm or right arm is registered (S1200).

Specifically, referring to FIGS. 2 and 12, when the registration of the first balance element of one (e.g., a right arm) of the user's left arm or right arm is requested depending on the user's key operation (S1210), the smart band 100 activates the motion sensor 208, and measures one (e.g., a right arm) of the user's left arm or right arm for a predetermined period of time to generate the motion data (S1220). For example, when the motion sensor 208 is an acceleration sensor, it measures the acceleration of the user's motion to generate the acceleration data, and when the motion sensor 208 is a gyroscope, it measures the rotational angular velocity of the user's motion to generate the angular velocity data. Here, the acceleration data includes the three-axis (x, y and z-axis) acceleration components, and the angular velocity data includes the three-axis angular velocity components.

Next, the sign of the motion data is determined (S1230).

Specifically, the control unit 202 may check whether the user's motion is the user's left arm motion or the right arm motion to determine the sign of the motion data.

Next, the integral values of the first to third rotational angular velocities are extracted (S1240).

First, the control unit 202 filters the noise of the rotational angular velocity data among the motion data having the determined sign (at this time, the nose may be filtered by a filter (not illustrated) included in the control unit 202), corrects the angular velocity data in which the noise is filtered by reflecting the rotational angle measured by an acceleration sensor (not illustrated), and may extract the integral values of the first to third rotational angular velocities by integrating the corrected rotational angular velocity.

Referring to FIGS. 2 and 13 again, a rotation matrix is generated (S1250).

The control unit 202 filters the noise of the extracted integral values of the first to third rotational angular velocities (at this time, the noise may be filtered by a filter (not illustrated) included in the control unit 202), and may generate a rotation matrix by utilizing the filtered integral values of the first to third rotational angular velocities.

Referring to FIGS. 2 and 13 again, the linear acceleration is calculated (S1260).

Specifically, the control unit 202 may calculate the linear acceleration, by applying the rotation matrix to the acceleration data among the motion data measured by the motion sensor 208.

Next, the first balance element is extracted and registered (S1270).

The control unit 202 integrates the linear acceleration to calculate the velocity and displacement values, performs Fourier transformation of the integral value of the third rotational angular velocity, and may extract the first balance element based on the velocity and displacement values, and the integral value of the third rotational angular velocity subjected to Fourier transformation. Further, the control unit 202 may register the extracted first balance element and store it in the memory 212.

Referring to FIGS. 2 and 12 again, after registering the first balance element of one (e.g., a right arm) of the user's left arm or right arm (S1200), the motion of the other (e.g., a left arm) of the user's left arm or right arm is determined (S1300).

Specifically, after registering the first balance element of one (e.g., a right arm) of the user's left arm or right arm (S1200), the motion sensor 208 is activated periodically or under the control of the control unit 202, and thus, the motion data may be generated by measuring the motion of the other (e.g., a left arm) of the user's left arm or right arm for a predetermined period of time. For example, when the motion sensor 208 is an acceleration sensor, it generates the acceleration data by measuring the acceleration of the user's motion, and when the motion sensor 208 is a gyroscope, it generates the angular velocity data by measuring the rotational angular velocity of the user's motion. Here, the acceleration data includes the three-axis (x, y and z-axis) acceleration components, and the angular velocity data includes the three-axis angular velocity components.

Next, the second balance element of the other (e.g., a left arm) of the user's left arm or right arm is extracted (S1400).

In order to extract the second balance element, first, the sign of the motion data is determined.

Specifically, the control unit 202 may determine the sign of the motion data, by checking whether the user's motion is the left arm motion or the right arm motion.

Next, the integral values of the first to third rotational angular velocities are extracted.

Specifically, first, the control unit 202 filters the noise of the rotational angular velocity data among the motion data having the determined sign (at this time, the nose may be filtered by a filter (not illustrated) included in the control unit 202), corrects the angular velocity data in which the noise is filtered by reflecting the rotational angle measured by an acceleration sensor (not illustrated), and may extract the integral values of the first to third rotational angular velocities by integrating the corrected rotational angular velocity.

Further, the rotation matrix is generated to extract the second balance element.

Specifically, the control unit 202 filters the noise of the extracted integral values of the first to third rotational angular velocities (at this time, the noise may be filtered by a filter (not illustrated) included in the control unit 202) and may generate a rotation matrix by utilizing the filtered integral values of the first to third rotational angular velocities.

Further, the linear acceleration is calculated to extract the second balance element.

Specifically, the control unit 202 may calculate the linear acceleration, by applying the rotation matrix to the acceleration data among the motion data measured by the motion sensor 208.

Next, the second balance element is extracted.

Specifically, the control unit 202 integrates the linear acceleration to calculate the velocity and displacement values, performs Fourier transformation of the integral value of the third rotational angular velocity, and may extract the second balance element, based on the velocity and displacement values, and the integral value of the third rotational angular velocity subjected to Fourier transformation.

Referring to FIGS. 2 and 12 again, after extracting the second balance element (S1400), the asymmetry index is calculated (S1500).

Specifically, the control unit 202 may calculate the asymmetry index based on a difference between the second balance element and the first balance element stored in the memory 208.

Next, the final score is calculated (S1600).

Specifically, the control unit 202 may calculate the spinal score, the shoulder score and the pelvic score based on the asymmetry index, and may calculate the final score based on the spinal score, the shoulder score and the pelvic score.

The final score calculated via such an algorithm may be displayed through the display unit 160, and a user may check which state the user's own body balance is in, through the final score.

For example, the higher the final score is, the better the body balance is, and the lower the final score is, the poor the body balance may be, but is not limited thereto.

Next, the smart band 100 finishes the algorithm according to an embodiment of the present invention.

The method for measuring the body balance of the smart band according to the embodiments of the invention may be embodied as a computer-readable code or program in a computer-readable recording medium. The computer-readable recording medium includes all kinds of recording devices that store data readable by a computer system. That is, the computer-readable recording medium may comprise program commands, data files, data structures and the like alone or in combination. The program commands recorded in the recording medium may be specifically designed and constructed for the present invention and may be known and available to a person having ordinary skill in the computer software art. Examples of the computer-readable recording medium are a ROM, a RAM, a CD-ROM, a magnetic tape, a floppy disk, an optical data storage device and the like, and also include those embodied in the form of carrier waves (e.g., data transmission through Internet). Also, the computer-readable recording medium may be distributed to a computer system connected to a network, and the computer-readable code may be stored and executed in a distributed manner.

The biometric authentication method of the wearable device may comprise wirelessly communicating with a first external device, and receiving a first request signal of a first external device.

At this time, the first external device may be in a first security state.

The biometric authentication method of the wearable device may comprise determining whether the wearable device is in a wearing state after receiving the first request signal; transmitting a non-wearing state information to the first external device when the wearable device is in the non-wearing state; collecting a first motion data generated by the user's motion through the motion sensor during a certain period of time or during collection of a certain amount of data when the wearable device is in a wearing state; transmitting the first motion data to the first external device; and receiving the first security level data and the second security level data from the first external device when the wearable device is in the wearing state.

At this time, the first external device may be in a second security state or a third security state. The biometric authentication method of the wearable device may comprise transmitting the non-wearing state information or the first state conversion information to the first external device when the wearable device is converted into the non-wearing state from the wearing state; and receiving only the first security level data from the first external device when the wearable device is in the non-wearing state.

At this time, the first external device may be in a fourth security or a fifth security state.

The first request signal may be a motion data request signal for registration of new biometric authentication information.

The first security state is a state in which the first external device is unlocked and the motion data for the wearer authentication of the wearable device is not registered.

The second security state may be a state in which the first external device is unlocked, the motion data for the wearer certification of the wearable device is registered, and the wearer authentication of the wearable device is completed.

The third security state may be a state in which the first external device is locked, the motion data for the wearer certification of the wearable device is registered, and the wearer authentication of the wearable device is completed.

The fourth security state may be a state in which the first external device is unlocked, the motion data for the wearer certification of the wearable device is registered, and the wearer authentication of the wearable device is not authenticated.

The fifth security state may be a state in which the first external device is locked, the motion data for the wearer certification of the wearable device is registered, and the wearer authentication of the wearable device is not authenticated.

The first motion data may be utilized as registration information for the wearer certification of the wearable device.

The first security level data may comprise at least one of the time information, the location information and the vibration or sound request information.

The second security level data may comprise at least one of at least a part of a telephone reception report information, a telephone caller information, a character message reception information, a character caller information, at least a part of the character content, schedule information, e-mail reception information, e-mail caller information and an e-mail content.

The biometric authentication method of the wearable device may comprise transmitting the wearing state information or the second state conversion information to the first external device when the wearable device is converted into the wearing state from the non-wearing state.

At this time, the first external device may be in a fourth security state or a fifth security state.

The biometric authentication method of the wearable device may comprise collecting a second motion data generated by the user's motion through the motion sensor during a certain period of time or during collection of a certain amount of data; receiving only the first security level data from the first external device in the wearing state of the wearable device; transmitting the second motion data to the first external device; and receiving the first security level data and the second security level data from the first external device.

At this time, the first external device may be in a second security state or a third security state.

The first motion data may comprise a plurality of feature points extracted from the information received from the motion sensor.

The first motion data transmitted to the first external device may extract a plurality of feature points from the first external device.

The first motion data may comprise a pair of collected motion data collected from the left and right arms or the left and right feet or left and right waists.

The first request signal may comprise a second request signal that requests the collection of the motion data from at least one of the left arm, the left foot and the left waist defined in the first external device, and a third request signal that requests the collection of the motion data from at least one of the right arm, the right foot and the right waist defined in the first external device.

After the second motion data is transmitted to the first external device, the first external device may determine whether the second motion data is the motion data of the left arm or the motion data of the right arm, the motion data of the left foot or the motion data of the right foot, and the motion data of the left waist or the motion data of the right waist.

The first external device may comprise a portable electronic device such as a smart phone, a smart pad, a notebook computer, a head mount display and a second wearable device.

The biometric authentication method of the portable electronic device may comprise wirelessly communicating with the wearable device, and transmitting a first request signal to the wearable device.

At this time, the portable electronic device may be in the first security state.

The biometric authentication method of the portable electronic device may comprise receiving the wearing state information of the wearable device from the wearable device; displaying a wearing guidance message when the wearable device is in the non-wearing state; receiving the first motion data collected through the motion sensor provided in the wearable device during a certain period of time or during collection of a certain amount of data when the wearable device is in a non-wearing state; and transmitting the first security level data and the second security level data to the wearable device when the wearable device is in a wearing state.

At this time, the portable electronic device may be in the second security state or the third security state.

The biometric authentication method of the portable electronic device may comprise receiving the wearing state information or the first state conversion information transmitted from the wearable device when the wearable device is converted into the non-wearing state from the wearing state; and transmitting only the first security level when the wearable device is in the non-wearing state. At this time, the portable electronic device may be in the fourth security state or a fifth security state.

The first request signal may be a motion data request signal for registration of new biometric authentication information.

The first security may be a state in which the portable electronic device is unlocked and the motion data for the wearer authentication of the wearable device is not registered.

The second security state may be a state in which the portable electronic device is unlocked, the motion data for the wearer authentication of the wearable device is registered, and the wearer authentication of the wearable device is completed.

The third security state may be a state in which the portable electronic device is locked, the motion data for the wearer authentication of the wearable device is registered, and the wearer authentication of the wearable device is completed.

The fourth security state may be a state in which the portable electronic device is unlocked, the motion data for the wearer authentication of the wearable device is registered, and the wearer authentication of the wearable device is not authenticated.

The fifth security state may be a state in which the portable electronic device is locked, the motion data for the wearer authentication of the wearable device is registered, and the wearer authentication of the wearable device is not authenticated.

The first motion data may be utilized as registration information for the wearer certification of the wearable device.

The first security level data may comprise at least one of the time information, the location information and the vibration or sound request information.

The second security level data may comprise at least one of at least a part of telephone reception report information, telephone caller information, character message reception information, character caller information, at least a part of the character content, schedule information, e-mail reception information, e-mail caller information and e-mail content.

The biometric authentication method of the wearable device may comprise receiving the wearing state information or the second state conversion information when the wearable device is converted into the wearing state from the non-wearing state.

At this time, the portable electronic device may be in the fourth security state or the fifth security state.

The biometric authentication method of the portable electronic device may comprise receiving the second motion data collected through the motion sensor provided in the wearable device during a certain period of time or during collection of a certain amount of data; transmitting only the first security level data when the wearable device is in the wearing state; receiving the second motion data; performing the authentication based on the first motion data and the second motion data; and transmitting the first security level data and the second security level data to the wearable device when the authentication is completed.

At this time, the portable electronic device may be in the second security state or the third security state.

The first motion data may comprise a plurality of feature points extracted from the information received from the motion sensor.

The first motion data received from the wearable device may extract a plurality of feature points from the portable electronic device.

The first motion data may comprise a pair of collected motion data collected from the left and right arms or the left and right feet or left and right waists.

The first request signal may comprise a second request signal that requests the collection of the motion data from at least one of the left arm, the left foot and the left waist defined in the portable electronic device, and a third request signal that requests the collection of the motion data from at least one of the right arm, the right foot and the right waist defined in the portable electronic device.

The portable electronic device may discriminate whether the received second motion data is the motion data of the left arm or the motion data of the right arm, the motion data of the left foot or the motion data of the right foot, and the motion data of the left waist or the motion data of the right waist.

The portable electronic device includes a communication module that wirelessly communicates with the wearable device, a display unit and a control unit. The control unit transmits the first request signal to the wearable device when the portable electronic device is in the first security state, receive the wearing state information from the wearable device to display the wearing guidance message when the wearable device is in the non-wearing state, receives the first motion data collected through the motion sensor provided in the wearable device during a certain period of time or during collection of a certain amount of data when the wearable device is in the wearing state, transmits the first security level data and the second security level data in the second security state or the third security state of the portable electronic device when the wearable device is in the wearing state, receives the non-wearing state information or the first state conversion information when the wearable device is converted into the non-wearing state from the wearing state, and may transmit only the first security level to the wearable device in the fourth security state or the fifth security state of the portable electronic device when the wearable device is in the non-wearing state.

The first motion data may comprise a plurality of feature points extracted from the information received from the motion sensor.

The received first motion data may extract a plurality of feature points from the portable electronic device.

The first motion data may comprise a pair of collected motion data collected from the left and right arms or the left and right feet or left and right waists.

The first request signal may comprise a second request signal that requests the collection of the motion data from at least one of the left arm, the left foot and the left waist defined in the portable electronic device, and a third request signal that requests the collection of the motion data from at least one of the right arm, the right foot and the right waist defined in the portable electronic device.

The authentication method of the portable electronic device may comprise wirelessly communicating with the wearable device; receiving the execution request of a first function requested by a user; requiring the first authentication; performing the first function when the first authentication is completed; receiving the execution request of a second function requested by a user; requesting the second authentication; performing the second function when the second authentication is completed; receiving the third authentication information from the wearable device; performing the third authentication based on the received third authentication information; requesting the first authentication when the third authentication is completed and the execution request of the first function is received and performing the first request when the first authentication is completed; and performing the second function without the second authentication request when the third authentication is completed and the execution request of the second function is received.

The portable electronic device may comprise transmitting a first request signal to the wearable device in the first security state.

The portable electronic device may comprise receiving the first motion data collected through the motion sensor provided in the wearable device during a certain period of time or during collection of a certain amount of data; and registering the first motion data.

The third authentication information may be a user's motion data that is collected through the motion sensor provided in the wearable device during a certain period of time or during collection of a certain amount of data when the wearable device is converted into the wearing state from the non-wearing state. At this time, the portable electronic device may be in a fourth security state or a fifth security state.

The first function may be a function of unlocking the portable electronic device.

The second function may be at least one of login of an application, unlocking of the locked content, the user authentication for electronic payment and the remote control of an external device.

The first authentication and the second authentication may be at least one of a password input, fingerprint recognition, iris recognition, touch pattern input, position information, time information, weight information, voice input and gesture input.

Performing the third authentication may compare a plurality of feature points of the first motion data with plurality of feature points of the third authentication information.

When the third function execution request is received in receiving the third function execution request from an external device, the portable electronic device requests the first authentication and the second authentication in the case of incompletion of the third authentication, and performs the third function in the case of completion of the first authenticate and the second authentication. Further, when the third function execution request is received, in the case of completion of the third function, the portable electronic device may perform the third function without request for the first authenticate and the second authentication.

The third authentication may release the third authentication when the wearing state of the wearable device is changed.

The first security state may be a state in which the portable electronic device is unlocked and the motion data for the wearer authentication of the wearable device is not unregistered. The fourth security state may be a state in which the portable electronic device is unlocked, the motion data for the wearer authentication of the wearable device is registered, and the wearer authentication of the wearable device is not authenticated.

The fifth security state may be a state in which the portable electronic device is locked, the motion data for the wearer certification of the wearable device is registered, and the wearer authentication of the wearable device is not authenticated.

When the fourth function execution request is received in receiving the fourth function execution request from an external device, the portable electronic device may request the wearable device for the third authentication in the case of incompletion of the third authentication. Further, when the fourth function execution request is received, in the case of completion of the third function, the portable electronic device may perform the fourth function only when both the first authenticate and the second authentication are completed.

The portable electronic device includes a communication module that wirelessly communicates with the wearable device, and the control unit. The control unit may request the first authentication when receiving the execution request of the first function requested by a user, and may perform the first function when the first authentication is completed.

The control unit may request the second authentication when receiving the execution request of the second function requested by the user, and may perform the second function when the second authentication is completed.

The control unit may perform the third authentication based on the received third authentication information when receiving the third authentication information from the wearable device.

The control unit may request the first authentication when the third authentication is completed and the execution request of the first function is received, and may perform the first function when the first authentication is completed.

The control unit may perform the second function without the second authentication request when the third authentication is completed and the execution request of the second function is received.

The control unit transmits the first request signal to the wearable device in the first security state of the portable electronic device, and may register the first motion data, by receiving the first motion data collected through the motions sensor provided in the wearable device during a certain amount or during collection of a certain amount of data.

The third authentication information may be a user's motion data collected through the motion sensor provided in the wearable device during a certain period of time or during collection of a certain amount of data when the wearable device is converted into the wearing state from the non-wearing state. At this time, the portable electronic device may be in a fourth security state or a fifth security state.

The control unit may request the first authentication and the second authentication in the case of incompletion of the third authentication when receiving the third function execution request from an external device, and may perform the third function request when the first authentication and the second authentication are completed.

The control unit may perform the third function without request for the first authentication and the second authentication, in the case of completion of the third authentication when the third function execution request is received.

When the fourth function execution request is received from an external device, in the case of incompletion of the third authentication, the control unit may request the wearable device for the third authentication. When the fourth function execution request is received, in the case of completion of the third authentication, the control unit may perform the fourth function only when both the first authentication and the second authentication are completed.

A method of correcting a posture of a wearable device may comprise wirelessly communicating with a portable electronic device; and receiving a first request signal of the portable electronic device.

At this time, the portable electronic device may be in a first security state.

The method for correcting the posture of the wearable device may further comprise collecting a first motion data generated by the user's motion through a motion sensor provided in the wearable device during a certain period of time or during collection of a certain amount of data; transmitting the first motion data to the portable electronic device; and receiving a second request signal of the portable electronic device.

At this time, the portable electronic device may be in a second security state.

The method for correcting the posture of the wearable device may further comprise collecting a second motion data generated by the user's motion through a motion sensor provided in the wearable device during a certain period of time or during collection of a certain amount of data; transmitting the second motion data to the portable electronic device; and receiving a third request signal of the portable electronic device.

At this time, the portable electronic device may be in a third security state.

The method for correcting the posture of the wearable device may further comprise collecting a third motion data generated by the user's motion through a motion sensor provided in the wearable device during a certain period of time or during collection of a certain amount of data; and transmitting the third motion data to the portable electronic device.

The portable electronic device stores the first motion data, the second motion data and the third motion data, the first motion data is deleted by a separate deletion command of a user, the second motion data and the third motion data may be automatically deleted by the portable electronic device when corresponding to pre-defined conditions.

When a difference over the pre-defined threshold occurs in comparison of the third motion data with the first motion data in the third security state of the portable electronic device, an alarm may be provided to the portable electronic device or the wearable device.

The pre-defined conditions may be at least one of pre-defined time, pre-defined amount of data, after derivation of pre-defined arithmetic value, and after determination of data compatibility.

Comparison between the third motion data and the first motion data may be performed by the wearable device.

Comparison between the third motion data and the first motion data may be performed by the portable electronic device.

The wearable device further comprises receiving a standard motion data through a network, when the difference over the pre-defined threshold occurs in comparison of the second motion data with the standard motion data, an alarm may be provided to the portable electronic device or the wearable device.

The portable electronic device receives and stores the standard motion data through the network, and when a difference over the pre-defined threshold in comparison to the second motion data occurs, an alarm may be provided to the portable electronic device or the wearable device.

The first security state may be a state in which the portable electronic device is unlocked and the user's first motion data is not registered.

The second security state may be a state in which the portable electronic device is unlocked and the user's first motion data is registered.

The third security state may be a state in which the portable electronic device is locked and the user's first motion data is registered.

The first motion data, the second motion data and the third motion data may comprise a plurality of feature points extracted from the information collected from the motion sensor.

The plurality of feature points of the first motion data, the second motion data and the third motion data may be extracted from the portable electronic device.

The first motion data may be used as model data for comparison with the motion data that is registered in the wearable device or the portable electronic device and is collected and received later.

The first motion data may update the first motion data, by additionally using the user's motion data collected after the first registration.

The standard motion data may include at least one of virtual standard walking motion data, golf swing motion data, swimming motion data, running motion data, gymnastics motion data and sports motion data.

The standard motion data may differ depending on at least one of the user's height, weight, age, sex and body image.

The wearable device includes a wireless communication unit that wirelessly communicates with a portable electronic device, a motion sensor unit that collects the user's motion data, and a control unit. The control unit receives a first request signal of the portable electronic device in the first security state of the portable electronic device, collects the first motion data generated by the user's motion through the motion sensor provided in the wearable device during a certain period of time or during collection of a certain amount of data, and may transmit the first motion data to the portable electronic device.

The control unit receives the second request signal in the second security state of the portable electronic device, collects the second motion data generated by the user's motion through the motion sensor provided in the wearable device during a certain period of time or during collection of a certain amount of data, and may transmit the second motion data to the portable electronic device.

The control unit receives the third request signal in the third security state of the portable electronic device, collects the third motion data generated by the user's motion through the motion sensor provided in the wearable device during a certain period of time or during collection of a certain amount of data, and may transmit the third motion data to the portable electronic device.

When a difference over the pre-defined threshold occurs in comparison of the third motion data with the first motion data in the third security state of the portable electronic device, an alarm may be provided to the portable electronic device or the wearable device.

The wearable device further comprises receiving a standard motion data through a network, and when a difference over the pre-defined threshold occurs in comparison of the second motion data with the standard motion data, an alarm may be provided to the portable electronic device or the wearable device.

The method for measuring left and right balance of the portable electronic device may comprise wirelessly communicating with a wearable device, and receiving the first motion data generated by the user's motion through a motion sensor provided in the wearable device during a certain period of time or during collection of a certain amount of data.

At this time, the portable electronic device may be in a first security state.

The method for measuring the left and right balance of the portable electronic device may comprise second collecting the motion data generated by the user's motion through a motion sensor provided in the wearable device during a certain period of time or during collection of a certain amount of data.

At this time, the portable electronic device may be in a second security state.

The method for measuring the left and right balance of the portable electronic device may comprise outputting the comparison results of the received first and the second motion data in a third security state.

The method for measuring the left and right balance of the portable electronic device may comprise collecting a third motion data generated by the user's motion through a motion sensor provided in the wearable device during a certain period of time or during collection of a certain amount of data, and at this time, the portable electronic device may be in a fourth security state.

The portable electronic device may receive the third motion data earlier than the first motion data.

The method for measuring the left and right balance of the portable electronic device may comprise receiving a wearing state of the wearable device, receiving a wearing plan state of the wearable device, and transmitting a signal to provide a report that recommends left-wearing or right-wearing to the wearable device.

The wearing plan state may be a state in which the user motion over the pre-defined threshold is detected by the motion sensor in the non-wearing state.

The method for measuring the left and right balance of the portable electronic device may comprise counting a collection period of the first motion data, and transmitting a signal to provide a report that recommends the left-wearing or the right-wearing of the wearable device, depending on whether the collection period of the first motion data satisfies the pre-defined period.

The method for measuring the left and right balance of the portable electronic device may comprise determining an amount of collection of the first motion data, and transmitting a signal to provide a report that recommends the left-wearing or the right-wearing of the wearable device, depending on whether the amount of collection of the first motion data satisfies the pre-defined amount.

The report includes at least one of visual, audible and tactile reports, and in the method of providing the report, an output direction of the report may be determined using the motion sensor.

The method for measuring the left and right balance of the portable electronic device may further comprise determining the wearing direction whether the user wears the wearable device on a right side or a left side based on a part of the received motion data.

The method for measuring the left and right balance of the portable electronic device may add the motion data collected through the motion sensor to the first motion data or the second motion data depending on the wearing direction.

The first security state may be a state in which the portable electronic device is locked, the first motion data is registered and the second motion data is not registered.

The second security state may be a state in which the portable electronic device is locked, and the first motion data and the second motion data are registered.

The third security state may be a state in which the portable electronic device is unlocked, and the first motion data and the second motion data are registered.

The fourth security state may be a state in which the portable electronic device is locked, and the first motion data and the second motion data are not registered.

The first motion data and the second motion may comprise a plurality of feature points extracted from the information received from the motion sensor.

The plurality of feature points of the first motion data and the second motion data may be extracted from the portable electronic device.

The method for measuring the left and right balance of the portable electronic device may comprise wirelessly communicating with the wearable device, and receiving the first motion data generated by the user's motion through a motion sensor provided in a first wearable device during a certain period of time or during collection of a certain amount of data. At this time, the portable electronic device may be in a first security state The method for measuring the left and right balance of the portable electronic device may comprise receiving the second motion data generated by the user's motion through a motion sensor provided in a second wearable device during a certain period of time or during collection of a certain amount of data. At this time, the portable electronic device may be in a first security state.

The portable electronic device may output a comparison result of the transmitted first and the second motion data in the third security state.

The method for measuring the left and right balance of the portable electronic device may comprise performing wireless communication between the first wearable device and the second wearable device, and in transmitting the second motion data to the portable electronic device, the second wearable device may transmit the second motion data to the first wearable device and the first wearable device may transmit the second motion data to the portable electronic device.

The first wearable device and the second wearable device may be determined depending on whether the wearable device is worn on the user's right side or left side.

The portable electronic device includes a wireless communication unit that wirelessly communicates with a wearable device, a display unit and a control unit. The control unit may receive a first motion data, which collects the motion data generated by the user's motion through the motion sensor provided in the wearable device during a certain period of time or during collection of a certain amount of data, in the first security state.

The control unit receives a second motion data, which collects the motion data generated by the user's motion through the motion sensor provided in the wearable device during a certain period of time or during collection of a certain amount of data, in the second security state, and may output the comparison result of the transmitted first and second motion data in the third security state.

The control unit receives a third motion data, which collects the motion data generated by the user's motion through the motion sensor provided in the wearable device during a certain period of time or during collection of a certain amount of data, in the fourth security state, and may receive the third motion data earlier than the first motion data.

The control unit receives a wearing plan state of the wearable device and may transmit a signal to provide a report that recommends the left-wearing or the right-wearing of the wearable device.

The wearing plan state may be a state in which the user motion over the pre-defined threshold is detected by the motion sensor in the non-wearing state of the wearable device.

The method for measuring the left and right balance of the wearable device may comprise wirelessly communicating with the portable electronic device, collecting a first motion data generated by the user's motion through the motion sensor provided in the wearable device during a certain period of time or during collection of a certain amount of data, and transmitting the first motion data to the portable electronic device.

At this time, the portable electronic device may be in a first security state.

The method for measuring the left and right balance of the wearable device may comprise collecting a second motion data generated by the user's motion through a motion sensor provided in the wearable device during a certain period of time or during collection of a certain amount of data, and transmitting the second motion data to the portable electronic device in the second security state of the portable electronic device. The portable electronic device may output the comparison result of the transmitted first and second motion data in the third security state.

The method for measuring the left and right balance of the wearable device may comprise collecting a third motion data generated by the user's motion through a motion sensor provided in the wearable device during a certain period of time or during collection of a certain amount of data, and transmitting the third motion data to the portable electronic device in the fourth security state of the portable electronic device. The wearable device may transmit the third motion data to the portable electronic device earlier than the first motion data.

The method for measuring the left and right balance of the portable electronic device may comprise determining the wearing state of the wearable device, determining a wearing plan state of the wearable device, and providing a report that recommends the left-wearing or the right-wearing of the wearable device. The wearing plan state may be a state in which the user motion over the pre-defined threshold is detected by the motion sensor in the non-wearing state.

The method for measuring the left and right balance of the wearable device may comprise counting a collection period of the first motion data, and providing a report that recommends the left-wearing or the right-wearing of the wearable device, depending on whether the collection period of the first motion data satisfies the pre-defined period.

The method for measuring the left and right balance of the wearable device may comprise determining an amount of collection of the first motion data, and providing a report that recommends the left-wearing or the right-wearing of the wearable device, depending on whether the amount of collection of the first motion data satisfies the pre-defined amount.

The report includes at least one of visual, audible and tactile reports, and in the method of providing the report, an output direction of the report may be determined using the motion sensor.

The method for measuring the left and right balance of the wearable device may further comprise determining the wearing direction whether the user wears the wearable device on a right side or a left side based on a part of the collected motion data in the motion sensor.

The method for measuring the left and right balance of the wearable device may add the motion data collected through the wearable device to the first motion data or the second motion data depending on the wearing direction.

The first security state may be a state in which the portable electronic device is locked, the first motion data is registered and the second motion data is not registered.

The second security state may be a state in which the portable electronic device is locked, and the first motion data and the second motion data are registered.

The third security state may be a state in which the portable electronic device is unlocked, and the first motion data and the second motion data are registered.

The fourth security state may be a state in which the portable electronic device is locked, and the first motion data and the second motion data are not registered.

The first motion data and the second motion may comprise a plurality of feature points extracted from the information received from the motion sensor.

The plurality of feature points of the first motion data and the second motion data may be extracted from the portable electronic device.

The method for measuring the left and right balance of the wearable device may comprise wirelessly communicating with portable electronic device, receiving the first motion data generated by the user's motion through a motion sensor provided in a first wearable device during a certain period of time or during collection of a certain amount of data, and transmitting the first motion data to the portable electronic device.

At this time, the portable electronic device may be in a first security state.

The method for measuring the left and right balance of the wearable device may comprise collecting a second motion data generated by the user's motion through a motion sensor provided in a second wearable device during a certain period of time or during collection of a certain amount of data, and transmitting the second motion data to the portable electronic device in the first security state of the portable electronic device. The portable electronic device may output a comparison result of the transmitted first and the second motion data in the third security state.

The method for measuring the left and right balance of the wearable device may comprise performing wireless communication between the first wearable device and the second wearable device, and in transmitting the second motion data to the portable electronic device, the second wearable device may transmit the second motion data to the first wearable device, and the first wearable device may transmit the second motion data to the portable electronic device.

The first wearable device and the second wearable device may be determined depending on whether the wearable device is worn on the user's right side or left side.

The wearable device includes a wireless communication unit that wirelessly communicates with a portable electronic device, a motion sensing unit that senses the user's motion, and a control unit. The control unit collects a first motion data, which collects the motion data generated by the user's motion through the motion sensor provided in the wearable device during a certain period of time or during collection of a certain amount of data, and may transmit the first motion data to the portable electronic device in the first security state of the portable electronic device.

The control unit collects a second motion data, which collects the motion data generated by the user's motion through the motion sensor provided in the wearable device during a certain period of time or during collection of a certain amount of data, and may transmit the second motion data to the portable electronic device in the second security state of the portable electronic device. The portable electronic device may output the comparison result of the transmitted first and second motion data in the third security state.

The control unit collects a third motion data, which collects the motion data generated by the user's motion through the motion sensor provided in the wearable device during a certain period of time or during collection of a certain amount of data, and may transmit the third motion data to the portable electronic device in the fourth security state of the portable electronic device. The control unit may transmit the third motion data earlier than the first motion data.

The control unit may determine a wearing state of the wearable device and may determine a wearing plate state of the wearable device to provide a report that recommends the left-wearing or the right-wearing of the wearable device.

The wearing plan state may be a state in which the user motion over the pre-defined threshold is detected by the motion sensor in the non-wearing state.

In concluding the detailed description, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation.

What is claimed is:

1. A method for measuring left and right balance of a wearable device, the method comprising:
   wirelessly communicating with a portable electronic device;
   collecting a first motion data generated by a user's motion through a motion sensor provided in the wearable device during a certain period of time or during collection of a certain amount of data;
   transmitting the first motion data to the portable electronic device, the portable electronic device being in a first security state;
   collecting a second motion data generated by the user's motion through the motion sensor provided in the wearable device during a certain period of time or during collection of a certain amount of data; and
   transmitting the second motion data to the portable electronic device in a second security state of the portable electronic device, wherein the portable electronic device outputs a comparison result of the transmitted first and second motion data in a third security state, and wherein the first security state is a state in which the portable electronic device is locked, the second security state is a state in which the portable electronic device is locked, and the third security state is a state in which the portable electronic device is unlocked.

2. The method of claim 1, further comprising:

collecting a third motion data generated by the user's motion through the motion sensor provided in the wearable device during a certain period of time or during collection of a certain amount of data; and transmitting the third motion data to the portable electronic device in a fourth security state of the portable electronic device, wherein the wearable device transmits the third motion data earlier than the first motion data to the portable electronic device.

3. The method of claim 1, further comprising:

determining a wearing state of the wearable device;

determining a wearing plan state of the wearable device; and providing a report that recommends left-wearing or right-wearing of the wearable device, wherein the wearing plan state is a state in which the user motion over a pre-defined threshold is detected by the motion sensor in a non-wearing state.

4. The method of claim 3, further comprising:

counting a collection period of the first motion data; and providing a report that recommends the left-wearing or the right-wearing of the wearable device, depending on whether the collection period of the first motion data satisfies a pre-defined period.

5. The method of claim 3, further comprising:

determining an amount of collection of the first motion data; and providing a report that recommends the left-wearing or the right-wearing of the wearable device, depending on whether the amount of collection of the first motion data satisfies a pre-defined amount.

6. The method of claim 3, wherein the report includes at least one of visual, audible and tactile reports, and in providing the report, an output direction of the report is determined using the motion sensor.

7. The method of claim 2, further comprising:

determining a wearing direction whether a user wears the wearable device on a right side or a left side based on a part of the motion data collected in the motion sensor.

8. The method of claim 7, further comprising:

adding the motion data collected through the motion sensor to the first motion data or the second motion data depending on the wearing direction.

9. The method of claim 1, wherein the first motion data is registered and the second motion data is not registered.

10. The method of claim 1, wherein the first motion data and the second motion data are registered.

11. The method of claim 1, wherein the first motion data and the second motion data are registered.

12. The method of claim 2, wherein the fourth security state is a state in which the portable electronic device is locked, and the first motion data and the second motion data are not registered.

13. The method of claim 1, wherein the first motion data and the second motion data comprise a plurality of feature points extracted from information received from the motion sensor.

14. The method of claim 13, wherein the plurality of feature points of the first motion data and the second motion data is extracted from the portable electronic device.

15. A method for measuring left and right balance of a wearable device, the method comprising:

wirelessly communicating with a portable electronic device;

receiving a first motion data generated by a user's motion through a motion sensor provided in a first wearable device during a certain period of time or during collection of a certain amount of data;

transmitting the first motion data to the portable electronic device, the portable electronic device being in a first security state;

collecting a second motion data generated by the user's motion through the motion sensor provided in a second wearable device during a certain period of time or during collection of a certain amount of data; and transmitting the second motion data to the portable electronic device in a second security state of the portable electronic device, wherein the portable electronic device outputs a comparison result of the transmitted first and second motion data in a third security state, and wherein the first security state is a state in which the portable electronic device is locked, the second security state is a state in which the portable electronic device is locked, and the third security state is a state in which the portable electronic device is unlocked.

16. The method of claim 15, further comprising performing a wireless communication between the first wearable device and the second wearable device, and in transmitting the second motion data to the portable electronic device, the second wearable device transmits the second motion data to the first wearable device, and the first wearable device transmits the second motion data to the portable electronic device.

17. The method of claim 15, wherein the first wearable device and the second wearable device are determined depending on whether the wearable device is worn on the user's right side or left side.

18. A wearable device comprising:

a wireless communication unit that wirelessly communicates with a portable electronic device;

a motion sensing unit that senses user's motion; and a control unit, wherein the control unit collects a first motion data, which collects the motion data generated by the user's motion through a motion sensor provided in the wearable device during a certain period of time or during collection of a certain amount of data, and transmits the first motion data to the portable electronic device in a first security state of the portable electronic device, and wherein the control unit collects a second motion data, which collects the motion data generated by the user's motion through the motion sensor provided in the wearable device during a certain period of time or during collection of a certain amount of data, and transmits the second motion data to the portable electronic device in a second security state of the portable electronic device, and the portable electronic device outputs comparison result of the transmitted first and second motion data in a third security state, and wherein the first security state is a state in which the portable electronic device is locked, the second security state is a state in which the portable electronic device is locked, and the third security state is a state in which the portable electronic device is unlocked.

19. The wearable device of claim 18, wherein the control unit collects a third motion data, which collects the motion data generated by the user's motion through the motion sensor provided in the wearable device during a certain period of time or during collection of a certain amount of data, and transmits the third motion data to the portable electronic device in a fourth security state of the portable electronic device, the third motion data being transmitted to the portable electronic device earlier than the first motion data.

20. The wearable device of claim 18, wherein the control unit determines a wearing state of the wearable device and determines a wearing plan state of the wearable device to provide a report that recommends left-wearing or right-wearing of the wearable device, and the wearing plan state is a state in which the user motion over a pre-defined threshold is detected by the motion sensor in a non-wearing state.

* * * * *